US011814370B2

(12) United States Patent
Jones et al.

(10) Patent No.: US 11,814,370 B2
(45) Date of Patent: Nov. 14, 2023

(54) DEUTERATED N-(5-(2,3-DIHYDROBENZO[B][1,4]DIOXINE-6-CARBOXAMIDO)-2-FLUOR-jOPHENYL)-2-((4-ETHYLPIPERAZIN-1-YL)M-ETHYL)QUINOLINE-6-CARBOXAMIDE

(71) Applicant: Cancer Research Technology Limited, London (GB)

(72) Inventors: Keith Jones, Sutton (GB); Matthew D. Cheeseman, Sutton (GB); A. Elisa Pasqua, Sutton (GB); Michael J. Tucker, Sutton (GB)

(73) Assignee: CANCER RESEARCH TECHNOLOGY LIMITED, London (GB)

( * ) Notice: Subject to any disclaimer, the term of this patent is extended or adjusted under 35 U.S.C. 154(b) by 677 days.

(21) Appl. No.: 16/339,056

(22) PCT Filed: Oct. 6, 2017

(86) PCT No.: PCT/GB2017/053033
§ 371 (c)(1),
(2) Date: Apr. 3, 2019

(87) PCT Pub. No.: WO2018/065787
PCT Pub. Date: Apr. 12, 2018

(65) Prior Publication Data
US 2020/0039965 A1 Feb. 6, 2020

(30) Foreign Application Priority Data
Oct. 7, 2016 (GB) ..................................... 1617103

(51) Int. Cl.
*C07D 405/12* (2006.01)
*C07B 59/00* (2006.01)
*A61P 35/00* (2006.01)

(52) U.S. Cl.
CPC .......... *C07D 405/12* (2013.01); *C07B 59/002* (2013.01); *A61P 35/00* (2018.01); *C07B 2200/05* (2013.01)

(58) Field of Classification Search
None
See application file for complete search history.

(56) References Cited

U.S. PATENT DOCUMENTS

| | | | |
|---|---|---|---|
| 5,137,805 | A | 8/1992 | Kingston et al. |
| 5,714,502 | A | 2/1998 | Prucher et al. |
| 5,756,343 | A | 5/1998 | Wu et al. |
| 6,455,520 | B1 | 9/2002 | Brown et al. |
| 6,867,036 | B1 | 3/2005 | Vile et al. |
| 9,701,664 | B2 * | 7/2017 | Jones ............... C07D 405/12 |
| 10,189,821 | B2 | 1/2019 | Jones et al. |
| 10,647,678 | B2 | 5/2020 | Jones et al. |
| 11,124,501 | B2 | 9/2021 | Jones et al. |
| 2002/0001629 | A1 | 1/2002 | Voellmy |
| 2002/0058679 | A1 | 5/2002 | Yokota et al. |
| 2005/0192219 | A1 | 9/2005 | Voellmy |
| 2005/0207972 | A1 | 9/2005 | Friebe et al. |
| 2006/0154278 | A1 | 7/2006 | Brody et al. |
| 2007/0105794 | A1 | 5/2007 | Lipinski et al. |
| 2007/0238682 | A1 | 10/2007 | Nudler et al. |
| 2009/0062222 | A1 | 3/2009 | Sherman et al. |
| 2009/0092600 | A1 | 4/2009 | Kufe |
| 2009/0117589 | A1 | 5/2009 | Southern |
| 2009/0163545 | A1 | 6/2009 | Goldfarb |
| 2010/0015605 | A1 | 1/2010 | Zucman-Rossi et al. |
| 2010/0216660 | A1 | 8/2010 | Nikolsky et al. |
| 2011/0112073 | A1 | 5/2011 | Thiele et al. |
| 2011/0123512 | A1 | 5/2011 | Prahlad et al. |
| 2011/0166038 | A1 | 7/2011 | Zhang et al. |
| 2011/0166058 | A1 | 7/2011 | Hinkle et al. |
| 2011/0182881 | A1 | 7/2011 | Chin et al. |
| 2011/0251096 | A1 | 10/2011 | Southern |
| 2011/0311508 | A1 | 12/2011 | Morimoto et al. |
| 2013/0133108 | A1 | 5/2013 | Warpeha et al. |
| 2014/0234858 | A1 | 8/2014 | Santagata et al. |
| 2014/0302042 | A1 | 10/2014 | Chin et al. |
| 2014/0315214 | A1 | 10/2014 | Taipale et al. |
| 2016/0289216 | A1 | 10/2016 | Jones et al. |
| 2017/0037036 | A1 | 2/2017 | Jones et al. |
| 2018/0093955 | A1 | 4/2018 | Jones et al. |
| 2019/0106413 | A1 | 4/2019 | Jones et al. |

FOREIGN PATENT DOCUMENTS

| | | |
|---|---|---|
| DE | 19531321 A1 | 2/1997 |
| EP | 0995745 A1 | 4/2000 |
| WO | WO-9601825 A1 | 1/1996 |
| WO | WO-1998017648 A1 | 4/1998 |
| WO | WO-9932433 A1 | 7/1999 |
| WO | WO-1999/59959 A1 | 11/1999 |
| WO | WO-2000007991 A1 | 2/2000 |

(Continued)

OTHER PUBLICATIONS

Tung, R. Future Med. Chem. 2016 vol. 8, pp. 491-494.*
Buteau et al., "Deuterated Drugs: Unexpectedly Unobvious?," J High Tech L, pp. 22-74 (2009).
International Search Report and Written Opinion for International Application No. PCT/GB2017/053033 dated Nov. 22, 2017.
AKos Screening Library (Aug. 20, 2013) Order No. AKOS006882384 and CHEMCATS accession No. 0097075038 (CAS Registry No. 1298093-46-5).
Ambinter Stock Screening Collection, published Sep. 15, 2014, Order No. Cat. Amb10715307.
Ambinter Stock Screening Collection, published Sep. 15, 2014, Order No. Cat. Amb8261001.

(Continued)

*Primary Examiner* — Amy C Bonaparte
(74) *Attorney, Agent, or Firm* — Goodwin Procter LLP

(57) ABSTRACT

The present invention relates to N-(5-(2,3-dihydrobenzo[b][1,4]dioxine-6-carboxamido)-2-fluorophenyl)-2-((4-ethylpiperazin-1-yl)methyl)quinoline-6-carboxamide, or a pharmaceutically acceptable salt or solvate thereof, wherein at least one hydrogen atom has been substituted with a deuterium atom. Other aspects include pharmaceutical compositions comprising said compounds and medical uses and methods of treatment using said compounds.

20 Claims, No Drawings

(56) References Cited

FOREIGN PATENT DOCUMENTS

| WO | WO-2000/18738 A1 | 4/2000 |
|---|---|---|
| WO | WO-0056341 A1 | 9/2000 |
| WO | WO-2000055153 A1 | 9/2000 |
| WO | WO-02/36576 A1 | 5/2002 |
| WO | WO-2003020227 A1 | 3/2003 |
| WO | WO-2004004703 A1 | 1/2004 |
| WO | WO-2004006858 A2 | 1/2004 |
| WO | WO-2004013117 A1 | 2/2004 |
| WO | WO-2004/019873 A2 | 3/2004 |
| WO | WO-2004/021988 A2 | 3/2004 |
| WO | WO-2004018414 A2 | 3/2004 |
| WO | WO-2004024083 A2 | 3/2004 |
| WO | WO-2004056774 A2 | 7/2004 |
| WO | WO-2005007151 A1 | 1/2005 |
| WO | WO-2005026334 A2 | 3/2005 |
| WO | WO-2005042496 A1 | 5/2005 |
| WO | WO-2006003378 A1 | 1/2006 |
| WO | WO-2006040568 A1 | 4/2006 |
| WO | WO-2006124874 A2 | 11/2006 |
| WO | WO-2007059157 A1 | 5/2007 |
| WO | WO-2008031534 A1 | 3/2008 |
| WO | WO-2008077165 A1 | 7/2008 |
| WO | WO-2008152013 A1 | 12/2008 |
| WO | WO-2009075874 A1 | 6/2009 |
| WO | WO-2010043631 A1 | 4/2010 |
| WO | WO-10053655 A2 | 5/2010 |
| WO | WO-2010093419 A1 | 8/2010 |
| WO | WO-11025167 A2 | 3/2011 |
| WO | WO-13030778 A2 | 3/2013 |
| WO | WO-13166427 A1 | 11/2013 |
| WO | WO-13172640 A1 | 11/2013 |
| WO | WO-14187959 A2 | 11/2014 |
| WO | WO-2015049535 A1 | 4/2015 |
| WO | WO-2016156872 A1 | 10/2016 |

OTHER PUBLICATIONS

Ashton et al., "New Low-Density Lipoprotein Receptor Upregulators Acting via a Novel Mechanism," J Med Chem, 39(17): 3343-3356 (1996).

Buteau, K., "Deurated Drugs: Unexpectedly Unobvious?" J. High Tech L., pp. 22-74 (2009).

Carpenter et al., "HSF1 as a Cancer Biomarker and Therapeutic Target," Curr. Cancer Drug Targets, 19(7):515-524 (2019).

Cheeseman et al., "Discovery of a Chemical Probe Bisamide (CCT251236): An Orally Bioavailable Efficacious Pirin Ligand from a Heat Shock Transcription Factor 1 (HSF1) Phenotypic Screen," J. Med. Chem., 60(1):180-201 (2017).

Chen et al., "Nucleoside analog inhibits microRNA-214 through targeting heat-shock factor 1 in human epithelial ovarian cancer," Cancer Sci, 104(12):1683-1689 (2013).

Dai et al., "Heat shock factor 1 is a powerful multifaceted modifier of carcinogenesis," Cell, 130:1005-1018 (2007).

Database PubChem Compound [Online] NCBI; Feb. 20, 2008 (Feb. 20, 2008). XP002731865. Database accession No. CID 23854223 abstract.

Dong et al., "Inhibiting Heat Shock Factor 1 in Cancer: A Unique Therapeutic Opportunity," Trends in Pharmacological Sciences 2019, 40 (12), 986-1005.

Dorwald., "Side Reaction in Organic Synthesis," A Guide to Successful Synthesis Design, Wiley-VCH, 1-15 (2005).

Jin et al., "Heat shock transcription factor 1 is a key determinant of HCC development by regulating hepatic steatosis and metabolic syndrome," Cell, 14:91-103 (2011).

Kim et al., "New Diarylureas and Diarylamides Possessing Acet(benz) amidophenyl Scaffold: Design, Synthesis, and Biorg. Med. and Antiproliferative Activty Against Melanoma Cell Line," Chem. Lett. 22:3269-3273 (2012).

Lee et al., "Synthesis of aminoquinazoline derivatives and their antiproliferative activities against melanoma cell line," Bioorgan Med Chem Lee, 20(19): 5722-5725 (2010).

Mendillo et al., "HSF1 drives a transcriptional program distinct from heat shock to support highly malignant human cancers," Cell, 150:549-562 (2012).

Mustafi et al., "Modulation of Akt and ERK1/2 pathways by resveratrol in chronic myelogenous leukemia (CML) cells results in the downregulation of Hsp70," PLoS One, 5(1):e8719 (2010).

Neustadt et al., "Combinatorial Libraries Based on a Novel and Readily Accessible "Centroid" Scaffold," Tetrahedron Lett, 39(30): 5317-5320 (1998).

Niume et al., "Heat-Resistant Polymers with Thianthrene Analog Units. II. Aromatic Polyamides," J Polym Sci, 18(7): 2163-2174 (1980).

TimTec Stock Building Blocks and Screening Compounds, published May 16, 2014, Order No. Cat. ST50925835.

Velayutham et al. Frontiers in Oncology 2018, vol. 8, article 97, p. 1-5.

Venkatesh et al., "Role of the Development Scientist in Compound Lead Selection and Optimization," Journal of Pharmaceutical Sciences, 89(2):145-154 (2000).

Whitesell et al., "Inhibiting the Transcript Factor HSF1 as an Anticancer Strategy," Expert Opinion Ther. Targets 13(4):469-478 (2009).

Zhou et al., "Synthesis and SAR of novel, non-MPEP chemotype mGluR5 NAMs identified by functional HTS," Bioorgan Med Chem Lett, 19(23): 6502-6506 (2009).

International Search Report and Written Opinion in PCT/GB2014/052992, dated Nov. 18, 2014 9 pages.

International Search Report and Written Opinion in PCT/GB2016/050938, dated May 18, 2016 12 pages.

International Search Report and Written Opinion in PCT/GB2017/053033, dated Nov. 22, 2017 10 pages.

U.S. Appl. No. 17/406,640, filed Aug. 19, 2021, 260 pgs.

U.S. Pat. No. 9,701,664, issued on Jul. 11, 2017; U.S. Appl. No. 15/026,911; published as US 2016-0289216 A1 on Oct. 6, 2016, Fused 1,4-Dihydrodioxin Derivatives as Inhibitors of Heat Shock Transcription Factor 1.

U.S. Pat. No. 10,189,821, issued on Jan. 29, 2019; U.S. Appl. No. 15/332,472; published as US 2017-0037036 A1 on Feb. 9, 2017, Fused 1,4-Dihydrodioxin Derivatives as Inhibitors of Heat Shock Transcription Factor 1.

U.S. Pat. No. 11,124,501, issued on Sep. 21, 2021; U.S. Appl. No. 16/212,455; published as US 2019-0106413 A1 on Apr. 11, 2019, Fused 1,4-Dihydrodioxin Derivatives as Inhibitors of Heat Shock Transcription Factor 1.

U.S. Appl. No. 17/406,640, filed Aug. 19, 2021, Fused 1,4-Dihydrodioxin Derivatives as Inhibitors of Heat Shock Transcription Factor 1.

U.S. Pat. No. 10,647,678, issued on May 12, 2020; U.S. Appl. No. 15/563,501; published as US 2018-0093955 A1 on Apr. 5, 2018, Quinoline Derivatives as Inhibitors of Heat Shock Factor 1 Pathway Activity.

\* cited by examiner

DEUTERATED N-(5-(2,3-DIHYDROBENZO[B][1,4] DIOXINE-6-CARBOXAMIDO)-2-FLUOROPHE-NYL)-2-((4-ETHYLPIPERAZIN-1-YL)METHYL) QUINOLINE-6-CARBOXAMIDE

Related Applications

This application is a § 371 national-stage application based on Patent Cooperation Treaty Application serial number PCT/GB2017/053033, filed Oct. 6, 2017; which claims the benefit of priority to United Kingdom Patent Application No. GB 1617103.5, filed on Oct. 7, 2016.

INTRODUCTION

The present invention relates to novel deuterated compounds that act as inhibitors of heat shock factor 1 (HSF1) activity. The present invention further relates to processes for preparing the compounds defined herein, to pharmaceutical compositions comprising them, and to their use in the treatment of HSF1-mediated conditions or diseases (such as cancer, autoimmune diseases and viral diseases).

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the identification of a number of molecular targets associated with key metabolic pathways that are known to be associated with malignancy.

Heat shock factor 1 (HSF1) is one such target molecule. HSF1 is the master regulator of the heat shock response, in which multiple genes are induced in response to temperature increase and other stresses. At non-shock temperatures in humans and other vertebrates, HSF1 is produced constitutively, but is inactive and bound by protein HSP90. At an elevated temperature, HSF1 is released by HSP90, moves from the cytoplasm to the nucleus, and trimerizes. This active HSF1 form binds to sequences called heat shock elements (HSE) in DNA and activates transcription of heat shock genes by RNA polymerase II. The HSE has a consensus sequence of three repeats of NGAAN and is present in the promoter regions of the HSP90, HSP70 and HSP27 genes. During cessation of the heat shock response, HSF1 is phosphorylated by mitogen-activated protein kinases (MAPKs) and glycogen synthase kinase 3 (GSK3) and returns to an inactive state. The biochemistry of HSF1 is described in more detail in, inter alia, Chu et al. 1996 J. Biol. Chem. 271:30847-30857 and Huang et al. 1997 J. Biol. Chem. 272:26009-26016.

HSF1 also interacts with additional factors. For example, HSF1 binds to DNA-dependent protein kinase (DNA-PK), which is involved in DNA repair. HSF1 is also target of mitogen-activated protein kinases, and its activity is down-regulated when the RAS signalling cascade is active.

Additional heat shock factor proteins in humans include HSF2, HSF3, and HSF4. HSF1, HSF2, and HSF3 are all positive regulators of heat shock gene expression, while HSF4 is a negative regulator. HSF1, HSF2 and HSF4 play a role in transcriptional control of other heat shock proteins. The various HSF proteins share about 40% sequence identity.

HSF1 activity has been implicated in several diseases, including cancer, and autoimmune, and viral diseases. HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g., promyelocytic leukemia), and Hodgkin's disease.

Accordingly, there is need for pharmacologically active agents that are capable of inhibiting HSF1. Such agents are potentially useful chemotherapeutic agents for the treatment of diseases or conditions in which HSF1 activity is mediated.

Furthermore, the efficacy of pharmacological agents in vivo may be hampered by poor absorption, distribution, metabolism and/or excretion (ADME) properties. For instance, if a pharmacological agent is rapidly metabolised, the agent will be cleared before it has chance to effectively modulate its target.

The present invention provides alternative or improved agents capable of inhibiting HSF1 which optionally demonstrate one or more ADME properties (e.g. clearance, metabolic stability, half-life, volume of distribution, bioavailability) indicating suitability for in vivo administration, particularly in vivo administration to humans. In certain embodiments, the compounds of the present invention demonstrate an improved ADME property (e.g. clearance, metabolic stability, half-life, volume of distribution, bioavailability) compared to undeuterated analogues.

SUMMARY OF THE INVENTION

In one aspect, the present invention relates to N-(5-(2,3-dihydrobenzo[b][1,4]dioxine-6-carboxamido)-2-fluorophenyl)-2-((4-ethylpiperazin-1-yl)methyl)quinoline-6-carboxamide, or a pharmaceutically acceptable salt or solvate thereof, wherein at least one hydrogen atom has been substituted with a deuterium atom.

In another aspect, the present invention provides a compound of formula (I), or a pharmaceutically acceptable salt or solvate thereof, as defined herein.

In another aspect, the present invention provides a pharmaceutical composition which comprises a compound of formula (I) as defined herein, or a pharmaceutically acceptable salt or solvate thereof, and one or more pharmaceutically acceptable excipients.

In another aspect, the present invention provides a compound of formula (I) as defined herein, or a pharmaceutically acceptable salt or solvate thereof, or a pharmaceutical composition as defined herein, for use in therapy.

In another aspect, the present invention provides a compound of formula (I) as defined herein, or a pharmaceutically acceptable salt or solvate thereof, or a pharmaceutical composition as defined herein, for use in the treatment of HSF1-mediated conditions or diseases (for example, cancer, autoimmune diseases or viral diseases).

In another aspect, the present invention provides a compound of formula (I) as defined herein, or a pharmaceutically acceptable salt or solvate thereof, or a pharmaceutical composition as defined herein, for use in the treatment of a proliferative condition.

In another aspect, the present invention provides a compound of formula (I) as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound of formula (I) as defined herein, or a pharmaceutically acceptable salt or solvate thereof, or a pharmaceutical composition as defined herein, for use in the production of a HSF1 inhibitory effect.

In another aspect, the present invention provides the use of a compound of formula (I) as defined herein, or a pharmaceutically acceptable salt or solvate thereof, in the manufacture of a medicament for use in treatment of HSF1-mediated conditions or diseases (for example, cancer, autoimmune diseases or viral diseases).

In another aspect, the present invention provides the use of a compound of formula (I) as defined herein, or a pharmaceutically acceptable salt or solvate thereof, in the manufacture of a medicament for use in the treatment of a proliferative condition.

In another aspect, the present invention provides the use of a compound of formula (I) as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound of formula (I) as defined herein, or a pharmaceutically acceptable salt or solvate thereof, in the manufacture of a medicament for use in the production of a HSF1 inhibitory effect.

In another aspect, the present invention provides a method of inhibiting HSF1 in vitro or in vivo, said method comprising contacting a cell with an effective amount of a compound of formula (I) as defined herein, or a pharmaceutically acceptable salt or solvate thereof.

In another aspect, the present invention provides a method of inhibiting cell proliferation in vitro or in vivo, said method comprising contacting a cell with an effective amount of a compound of formula (I) as defined herein, or a pharmaceutically acceptable salt or solvate thereof.

In another aspect, the present invention provides a method of treating a HSF1-mediated condition or disease (for example, cancer, autoimmune diseases or viral diseases), in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating a proliferative disorder in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound of formula (I) as defined herein, or a pharmaceutically acceptable salt or solvate thereof, or a pharmaceutical composition as defined herein.

The present invention further provides a method of synthesising a compound of formula (I) as defined herein, or a pharmaceutically acceptable salt or solvate thereof.

In another aspect, the present invention provides a compound of formula (I) as defined herein, or a pharmaceutically acceptable salt or solvate thereof, obtainable by, or obtained by, or directly obtained by a method of synthesis as defined herein.

In another aspect, the present invention provides novel intermediates defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The phrase "compound of the invention" means those compounds which are disclosed herein, both generically and specifically.

In the compounds of the invention, unless explicitly stated otherwise, when a position is specifically designated as "H" or "hydrogen", the position would be understood to occupied by hydrogen at its natural isotopic abundance (e.g. about 99.98% $^1$H).

In the compounds of the invention, unless explicitly stated otherwise, when a position is specifically designated as "D" or "deuterium", the position would be understood by a skilled person to occupied by deuterium ($^2$H) at an isotopic abundance greater than its natural isotopic abundance (e.g. greater than about 0.015%).

In one embodiment, where a position is designated as "D" or "deuterium", the position would be understood to be occupied by deuterium at at least 3340 times its natural isotopic abundance. In one embodiment, a position designated D is occupied with deuterium at an isotopic purity of $^2$H of at least 50.1%. Isotopic purity can be determined using conventional analytical methods known to a person skilled in the art, including mass spectrometry and nuclear magnetic resonance spectroscopy.

In one embodiment, where a position is designated as "D" or "deuterium", the position would be understood to be occupied by deuterium at at least 4000 times its natural isotopic abundance. In one embodiment, a position designated D is occupied with deuterium at an isotopic purity of $^2$H of at least 60%.

In another embodiment, where a position is designated as "D" or "deuterium", the position would be understood to be occupied by deuterium at at least 4500 times its natural isotopic abundance. In one embodiment, a position designated D is occupied with deuterium at an isotopic purity of $^2$H of at least 67.5%.

In another embodiment, where a position is designated as "D" or "deuterium", the position would be understood to be occupied by deuterium at at least 5000 times its natural isotopic abundance. In one embodiment, a position designated D is occupied with deuterium at an isotopic purity of $^2$H of at least 75%.

In another embodiment, where a position is designated as "D" or "deuterium", the position would be understood to be occupied by deuterium at at least 5500 times its natural isotopic abundance. In one embodiment, a position designated D is occupied with deuterium at an isotopic purity of $^2$H of at least 82.5%.

In another embodiment, where a position is designated as "D" or "deuterium", the position would be understood to be occupied by deuterium at at least 6000 times its natural isotopic abundance. In one embodiment, a position designated D is occupied with deuterium at an isotopic purity of $^2$H of at least 90%.

In another embodiment, where a position is designated as "D" or "deuterium", the position would be understood to be occupied by deuterium at at least 6333.5 times its natural isotopic abundance. In one embodiment, a position designated D is occupied with deuterium at an isotopic purity of $^2$H of at least 95%.

In another embodiment, where a position is designated as "D" or "deuterium", the position would be understood to be occupied by deuterium at at least 6466.7 times its natural isotopic abundance. In one embodiment, a position designated D is occupied with deuterium at an isotopic purity of $^2$H of at least 97%.

In another embodiment, where a position is designated as "D" or "deuterium", the position would be understood to be occupied by deuterium at at least 6533.3 times its natural isotopic abundance. In one embodiment, a position designated D is occupied with deuterium at an isotopic purity of $^2$H of at least 98%.

In another embodiment, where a position is designated as "D" or "deuterium", the position would be understood to be occupied by deuterium at at least 6600 times its natural isotopic abundance. In one embodiment, a position designated D is occupied with deuterium at an isotopic purity of $^2$H of at least 99%.

In another embodiment, where a position is designated as "D" or "deuterium", the position would be understood to be occupied by deuterium at at least 6633.3 times its natural isotopic abundance. In one embodiment, a position designated D is occupied with deuterium at an isotopic purity of $^2$H of at least 99.5%.

In another embodiment, where a position is designated as "D" or "deuterium", the position would be understood to be occupied by deuterium at from 3340 times to 6633.3 times its natural isotopic abundance. In one embodiment, a position designated D is occupied with deuterium at an isotopic purity of $^2$H of from about 50.1% to about 99.5%.

In another embodiment, where a position is designated as "D" or "deuterium", the position would be understood to be occupied by deuterium at from 4000 times to 6633.3 times its natural isotopic abundance. In one embodiment, a position designated D is occupied with deuterium at an isotopic purity of $^2$H of from about 60% to about 99.5%.

In another embodiment, where a position is designated as "D" or "deuterium", the position would be understood to be occupied by deuterium at from 4500 times to 6633.3 times its natural isotopic abundance. In one embodiment, a position designated D is occupied with deuterium at an isotopic purity of $^2$H of from about 67.5% to about 99.5%.

In another embodiment, where a position is designated as "D" or "deuterium", the position would be understood to be occupied by deuterium at from 5000 times to 6633.3 times its natural isotopic abundance. In one embodiment, a position designated D is occupied with deuterium at an isotopic purity of $^2$H of from about 75% to about 99.5%.

In another embodiment, where a position is designated as "D" or "deuterium", the position would be understood to be occupied by deuterium at from 5500 times to 6633.3 times its natural isotopic abundance. In one embodiment, a position designated D is occupied with deuterium at an isotopic purity of $^2$H of from about 82.5% to about 99.5%.

In another embodiment, where a position is designated as "D" or "deuterium", the position would be understood to be occupied by deuterium at from 6000 times to 6633.3 times its natural isotopic abundance. In one embodiment, a position designated D is occupied with deuterium at an isotopic purity of $^2$H of from about 90% to about 99.5%.

In another embodiment, where a position is designated as "D" or "deuterium", the position would be understood to be occupied by deuterium at from 3340 times to 6533.3 times its natural isotopic abundance. In one embodiment, a position designated D is occupied with deuterium at an isotopic purity of $^2$H of from about 50.1% to about 98%.

In another embodiment, where a position is designated as "D" or "deuterium", the position would be understood to be occupied by deuterium at from 4000 times to 6533.3 times its natural isotopic abundance. In one embodiment, a position designated D is occupied with deuterium at an isotopic purity of $^2$H of from about 60% to about 98%.

In another embodiment, where a position is designated as "D" or "deuterium", the position would be understood to be occupied by deuterium at from 4500 times to 6533.3 times its natural isotopic abundance. In one embodiment, a position designated D is occupied with deuterium at an isotopic purity of $^2$H of from about 67.5% to about 98%.

In another embodiment, where a position is designated as "D" or "deuterium", the position would be understood to be occupied by deuterium at from 5000 times to 6533.3 times its natural isotopic abundance. In one embodiment, a position designated D is occupied with deuterium at an isotopic purity of $^2$H of from about 75% to about 98%.

In another embodiment, where a position is designated as "D" or "deuterium", the position would be understood to be occupied by deuterium at from 5500 times to 6533.3 times its natural isotopic abundance. In one embodiment, a position designated D is occupied with deuterium at an isotopic purity of $^2$H of from about 82.5% to about 98%.

In another embodiment, where a position is designated as "D" or "deuterium", the position would be understood to be occupied by deuterium at from 6000 times to 6533.3 times its natural isotopic abundance. In one embodiment, a position designated D is occupied with deuterium at an isotopic purity of $^2$H of from about 90% to about 98%.

In one embodiment, where a position is designated as "D" or "deuterium", the position designated D is occupied with deuterium at an isotopic purity of $^2$H of about 98%.

As used herein, "substituted with deuterium" refers to the replacement of one or more hydrogen atoms with a corresponding number of deuterium atoms.

Compounds of the Invention

In one aspect, the present invention relates to N-(5-(2,3-dihydrobenzo[b][1,4]dioxine-6-carboxamido)-2-fluorophenyl)-2-((4-ethylpiperazin-1-yl)methyl)quinoline-6-carboxamide, or a pharmaceutically acceptable salt or solvate thereof, wherein at least one hydrogen atom has been substituted with a deuterium atom.

In one aspect, the present invention relates to a compound of formula (I), or a pharmaceutically acceptable salt or solvate thereof,

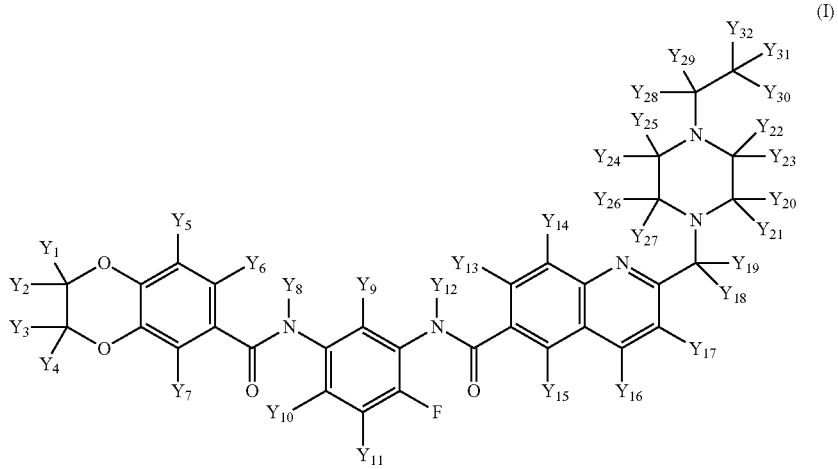

wherein $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are independently selected from hydrogen or deuterium, provided that at least one of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ is deuterium.

In one embodiment, at least 2, 3, 4, 5, 6, 7, 8, 9 or 10 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 20 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 18 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 16 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 14 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 13 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 12 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 11 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 10 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 9 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 8 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 7 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 6 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 5 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 4 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 3 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

Suitably, from 4 to 10 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

Suitably from 4 to 8 of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In one embodiment, $Y_8$ and $Y_{12}$ are hydrogen.
In another embodiment, $Y_5$, $Y_6$ and $Y_7$ are hydrogen.
In another embodiment, $Y_9$, $Y_{10}$ and $Y_{11}$ are hydrogen.
In another embodiment, $Y_{13}$, $Y_{14}$ and $Y_{15}$ are hydrogen.

In another embodiment, $Y_{16}$ and $Y_{17}$ are hydrogen.

In another embodiment, $Y_{18}$ and $Y_{19}$ are hydrogen.

In another embodiment, $Y_5$, $Y_6$, $Y_7$, $Y_8$ and $Y_{12}$ are hydrogen.

In another embodiment, $Y_{13}$, $Y_{14}$, $Y_{15}$, $Y_8$ and $Y_{12}$ are hydrogen.

In another embodiment, $Y_5$, $Y_6$, $Y_7$, $Y_{13}$, $Y_{14}$, $Y_{15}$, $Y_8$ and $Y_{12}$ are hydrogen.

In another embodiment, $Y_{13}$, $Y_{14}$, $Y_{15}$, $Y_{16}$, $Y_{17}$ $Y_8$, and $Y_{12}$ are hydrogen.

In another embodiment, $Y_5$, $Y_6$, $Y_7$, $Y_{13}$, $Y_{14}$, $Y_{15}$, $Y_{16}$, $Y_{17}$, $Y_8$, and $Y_{12}$ are hydrogen.

In another embodiment, $Y_9$, $Y_{10}$, $Y_{11}$, $Y_{13}$, $Y_{14}$, $Y_{15}$, $Y_8$ and $Y_{12}$ are hydrogen.

In another embodiment $Y_9$, $Y_{10}$, $Y_{11}$, $Y_{13}$, $Y_{14}$, $Y_{15}$, $Y_{16}$, $Y_{17}$, $Y_8$ and $Y_{12}$ are hydrogen.

In another embodiment, $Y_5$, $Y_6$, $Y_7$, $Y_9$, $Y_{10}$, $Y_{11}$, $Y_{13}$, $Y_{14}$, $Y_{15}$, $Y_{16}$, $Y_{17}$, $Y_8$ and $Y_{12}$ are hydrogen.

In one embodiment, at least one of $Y_1$, $Y_2$, $Y_3$, $Y_4$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ is deuterium.

In another embodiment, at least 2, 3, 4, 5, 6, 7, 8, 9 or 10 of $Y_1$, $Y_2$, $Y_3$, $Y_4$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 19 (suitably 1 to 17, suitably 1 to 15, suitably 1 to 13, suitably 1 to 12, suitably 1 to 11, suitably 1 to 10, suitably 1 to 9, suitably 1 to 8, suitably 1 to 7, suitably 1 to 6, suitably 1 to 5, suitably 1 to 4, suitably 1 to 3) of $Y_1$, $Y_2$, $Y_3$, $Y_4$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 4 to 10 (suitably 4 to 8) of $Y_1$, $Y_2$, $Y_3$, $Y_4$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In one embodiment, at least one of $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ is deuterium.

In another embodiment, at least 2, 3, 4, 5, 6, 7, 8, 9 or 10 of $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 1 to 17 (suitably 1 to 15, suitably 1 to 13, suitably 1 to 12, suitably 1 to 11, suitably 1 to 10, suitably 1 to 9, suitably 1 to 8, suitably 1 to 7, suitably 1 to 6, suitably 1 to 5, suitably 1 to 4, suitably 1 to 3) of $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, from 4 to 10 (suitably 4 to 8) of $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In one embodiment, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$ and $Y_{17}$ are hydrogen; and $Y_1$, $Y_2$, $Y_3$, $Y_4$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are independently selected from hydrogen and deuterium.

In another embodiment, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$ and $Y_{19}$ are hydrogen; and $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are independently selected from hydrogen and deuterium.

In one embodiment, $Y_1$ and $Y_2$ are deuterium.

In another embodiment, $Y_3$ and $Y_4$ are deuterium.

In another embodiment, $Y_{18}$ and $Y_{19}$ are deuterium.

In another embodiment, $Y_{24}$, $Y_{25}$, $Y_{26}$ and $Y_{27}$ are deuterium.

In another embodiment, $Y_{20}$, $Y_{21}$, $Y_{23}$ and $Y_{24}$ are deuterium.

In another embodiment, $Y_{20}$, $Y_{21}$, $Y_{26}$ and $Y_{27}$ are deuterium.

In another embodiment, $Y_{22}$, $Y_{23}$, $Y_{24}$ and $Y_{25}$ are deuterium.

In another embodiment, $Y_{28}$ and $Y_{29}$ are deuterium.

In another embodiment, $Y_{30}$, $Y_{31}$ and $Y_{32}$ are deuterium.

In another embodiment, $Y_1$, $Y_2$, $Y_3$ and $Y_4$ are deuterium.

In another embodiment, $Y_{20}$, $Y_{21}$, $Y_{22}$, $Y_{23}$, $Y_{24}$, $Y_{25}$, $Y_{26}$ and $Y_{27}$ are deuterium.

In another embodiment, $Y_{28}$, $Y_{29}$, $Y_{30}$, $Y_{31}$ and $Y_{32}$ are deuterium.

In another embodiment, $Y_1$, $Y_2$, $Y_3$, $Y_4$ $Y_{28}$, $Y_{29}$, $Y_{30}$, $Y_{31}$ and $Y_{32}$ are deuterium.

In another embodiment, $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$ and $Y_{27}$ are deuterium.

In another embodiment, $Y_1$, $Y_2$, $Y_3$, $Y_4$, $Y_{28}$, $Y_{29}$, $Y_{30}$, $Y_{31}$ and $Y_{32}$ are deuterium.

In another embodiment, $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$ and $Y_{27}$ are deuterium.

In another embodiment, $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are deuterium.

In another embodiment, the compound of the invention is selected from any one of compounds 1 to 20 in the table below, or pharmaceutically acceptable salts or solvates thereof, wherein $Y_1$ to $Y_{32}$ have the meanings provided in the table:

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| $Y_1$ | D | H | D | H | H | H | H | H | H | H | H | D | D | D | D | D | H | H | D | D |
| $Y_2$ | D | H | D | H | H | H | H | H | H | H | H | D | D | D | D | D | H | H | D | D |
| $Y_3$ | H | D | D | H | H | H | H | H | H | H | H | D | D | D | D | D | H | H | D | D |
| $Y_4$ | H | D | D | H | H | H | H | H | H | H | H | D | D | D | D | D | H | H | D | D |
| $Y_5$ | H | H | H | H | H | H | H | H | H | H | H | H | H | H | H | H | H | H | H | H |
| $Y_6$ | H | H | H | H | H | H | H | H | H | H | H | H | H | H | H | H | H | H | H | H |
| $Y_7$ | H | H | H | H | H | H | H | H | H | H | H | H | H | H | H | H | H | H | H | H |
| $Y_8$ | H | H | H | H | H | H | H | H | H | H | H | H | H | H | H | H | H | H | H | H |
| $Y_9$ | H | H | H | H | H | H | H | H | H | H | H | H | H | H | H | H | H | H | H | H |
| $Y_{10}$ | H | H | H | H | H | H | H | H | H | H | H | H | H | H | H | H | H | H | H | H |
| $Y_{11}$ | H | H | H | H | H | H | H | H | H | H | H | H | H | H | H | H | H | H | H | H |
| $Y_{12}$ | H | H | H | H | H | H | H | H | H | H | H | H | H | H | H | H | H | H | H | H |
| $Y_{13}$ | H | H | H | H | H | H | H | H | H | H | H | H | H | H | H | H | H | H | H | H |
| $Y_{14}$ | H | H | H | H | H | H | H | H | H | H | H | H | H | H | H | H | H | H | H | H |
| $Y_{15}$ | H | H | H | H | H | H | H | H | H | H | H | H | H | H | H | H | H | H | H | H |
| $Y_{16}$ | H | H | H | H | H | H | H | H | H | H | H | H | H | H | H | H | H | H | H | H |
| $Y_{17}$ | H | H | H | H | H | H | H | H | H | H | H | H | H | H | H | H | H | H | H | H |
| $Y_{18}$ | H | H | H | H | H | H | H | H | D | D | D | H | D | H | D | H | D | H | D | D |
| $Y_{19}$ | H | H | H | H | H | H | H | H | D | D | D | H | D | H | D | H | D | H | D | D |
| $Y_{20}$ | H | H | H | D | H | D | H | H | H | H | H | H | H | D | D | D | D | D | D | D |

-continued

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| $Y_{21}$ | H | H | H | D | H | D | H | H | H | H | H | H | H | H | D | D | D | D | D | D |
| $Y_{22}$ | H | H | H | H | D | D | H | H | H | H | H | H | H | H | D | D | D | D | D | D |
| $Y_{23}$ | H | H | H | H | D | D | H | H | H | H | H | H | H | H | D | D | D | D | D | D |
| $Y_{24}$ | H | H | H | H | D | D | H | H | H | H | H | H | H | H | D | D | D | D | D | D |
| $Y_{25}$ | H | H | H | D | H | D | H | H | H | H | H | H | H | H | D | D | D | D | D | D |
| $Y_{26}$ | H | H | H | D | H | D | H | H | H | H | H | H | H | H | D | D | D | D | D | D |
| $Y_{27}$ | H | H | H | D | H | D | H | H | H | H | H | H | H | H | D | D | D | D | D | D |
| $Y_{28}$ | H | H | H | H | H | H | D | H | D | H | D | D | D | D | H | H | D | D | D | D |
| $Y_{29}$ | H | H | H | H | H | H | D | H | D | H | D | D | D | D | H | H | D | D | D | D |
| $Y_{30}$ | H | H | H | H | H | H | H | D | D | H | D | D | D | D | H | H | D | D | D | D |
| $Y_{31}$ | H | H | H | H | H | H | D | D | H | D | D | D | D | D | H | H | D | D | D | D |
| $Y_{32}$ | H | H | H | H | H | H | H | D | D | H | D | D | D | D | H | H | D | D | D | D |

In one embodiment, the compound of the invention is selected from compounds 3, 6, 9 and 11 to 20 in the table above, or pharmaceutically acceptable salts or solvates thereof.

In another embodiment, the compound of the invention is selected from compounds 3, 6, 9, 13, 15, 17 and 19 in the table above, or pharmaceutically acceptable salts or solvates thereof.

In another embodiment, the compound of the invention is selected from compounds 3, 6 and 9 in the table above, or pharmaceutically acceptable salts or solvates thereof.

In another embodiment, the compound of the invention is selected from:

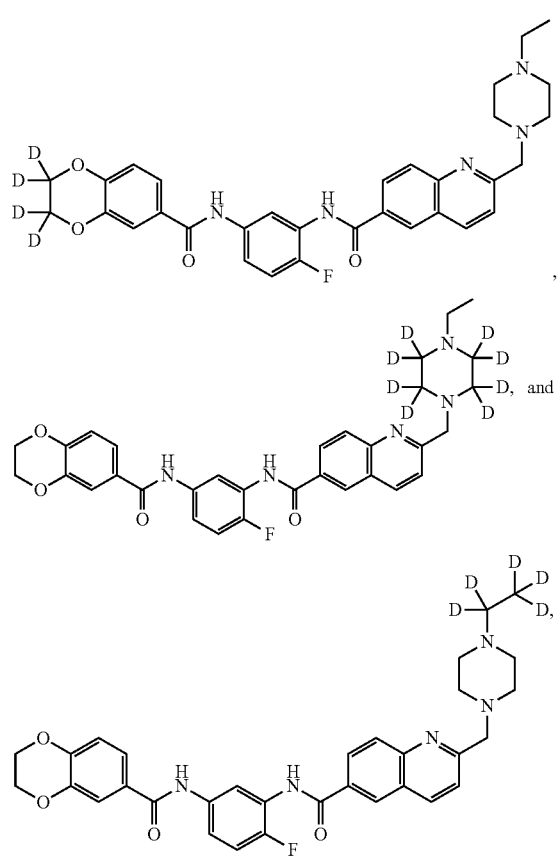

In another embodiment, the compound of the invention is

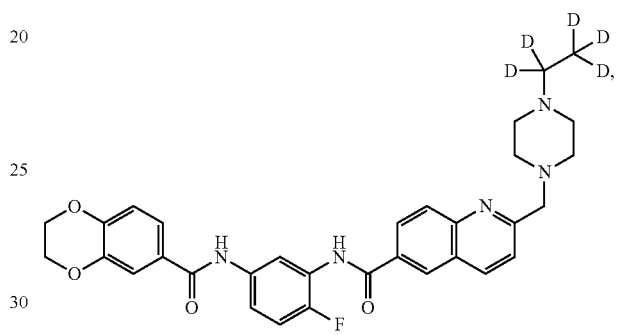

or a pharmaceutically acceptable salt or solvate thereof.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as or pharmaceutically acceptable salts and solvates thereof.

either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess HSF1 inhibitory activity.

The present invention also encompasses compounds of the invention as defined herein which comprise one or more further isotopic substitutions at position other than H. For example, C may be in any isotopic form including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess HSF1 inhibitory activity.

It is also to be understood that certain compounds of the invention may exhibit polymorphism, and that the invention encompasses all such forms that possess HSF1 inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

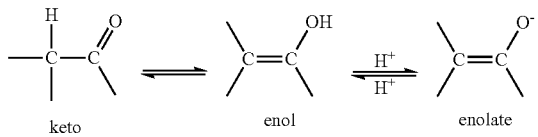

Compounds of the invention containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages 1779. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula (I) as defined hereinbefore when made available by organic synthesis and when made available within the human or animal body by way of cleavage of a pro-drug thereof. Accordingly, the present invention includes those compounds of the formula (I) that are produced by organic synthetic means and also such compounds that are produced in the human or animal body by way of metabolism of a precursor compound, that is a compound of the formula (I) may be a synthetically-produced compound or a metabolically-produced compound.

A suitable pharmaceutically acceptable pro-drug of a compound of the formula (I) is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula (I) that possesses a carboxy group is, for example, an in vivo cleavable ester thereof. An in vivo cleavable ester of a compound of the formula (I) containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula (I) that possesses a hydroxy group is, for example, an in vivo cleavable ester or ether thereof. An in vivo cleavable ester or ether of a compound of the formula (I) containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include o-acyloxyalkyl groups such as acetoxymethyl and pivaloyloxymethyl groups.

A suitable pharmaceutically acceptable pro-drug of a compound of the formula (I) that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula (I) that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula (I) may be exerted in part by one or more metabolites that are formed within the human or animal body after administration of a compound of the formula (I). As stated hereinbefore, the in vivo effects of a compound of the formula (I) may also be exerted by way of metabolism of a precursor compound (a pro-drug).

It shall also be appreciated that compounds of formula (I) may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described herein, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed, for, example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3.OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The compounds of the invention may be prepared using synthetic techniques that are known in the art (as illustrated in the examples herein).

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula (I) will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The compounds of the present invention function as inhibitors of HSF1 activity. Accordingly, the compounds of the invention are potentially useful agents for the treatment of diseases or conditions in which HSF1 activity is implicated.

In one aspect, the present invention provides a compound of formula (I), or a pharmaceutically acceptable salt or solvate thereof, or a pharmaceutical composition as defined herein for use in therapy.

In another aspect, the present invention provides a method of inhibiting HSF1 activity in a cell, the method comprising administering to said cell compound of formula (I) as defined herein, or a pharmaceutically acceptable salt or solvate thereof.

In a further aspect, the present invention provides a method of inhibiting HSF1 in vitro or in vivo, said method comprising contacting a cell with an effective amount of a compound, or a pharmaceutically acceptable salt or solvate thereof, as defined herein.

In another aspect, the present invention provides a method of inhibiting HSF1 activity in a human or animal subject in need of such inhibition, the method comprising administering to said subject an effective amount of a compound of formula (I) as defined herein, or a pharmaceutically acceptable salt or solvate thereof.

In another aspect, the present invention provides a compound of formula (I) as defined herein, or a pharmaceutically acceptable salt or solvate thereof for use in the treatment of disease or condition associated with HSF1 activity.

In another aspect, the present invention provides the use of a compound of formula (I) as defined herein, or a pharmaceutically acceptable salt or solvate thereof, in the manufacture of a medicament for use in the treatment of disease or condition associated with HSF1 activity.

In yet another aspect, the present invention provides a method of treating a proliferative disorder in a human or animal subject, the method comprising administering to said subject a therapeutically acceptable amount of a compound of formula (I) as defined herein, or a pharmaceutically acceptable salt or solvate thereof.

HSF1 activity has been implicated in several diseases, including cancer, and autoimmune, and viral diseases.

The broad activity of HSF1 and the role it plays in many disease states is discussed in the scientific literature, see for example:

Evans, C. G.; Chang, L.; Gestwicki, J. E., Heat Shock Protein 70 (Hsp70) as an Emerging Drug Target. *J Med Chem* 2010, 53 (12), 4585-4602;

Calderwood, S. K.; Khaleque, M. A.; Sawyer, D. B.; Ciocca, D. R., Heat shock proteins in cancer: chaperones of tumorigenesis. *Trends Biochem Sci* 2006, 31 (3), 164-172;

Dai, C.; Whitesell, L.; Rogers, A. B.; Lindquist, S., Heat shock factor 1 is a powerful multifaceted modifier of carcinogenesis. *Cell* 2007, 130 (6), 1005-1018;

Whitesell, L.; Lindquist, S., Inhibiting the transcription factor HSF1 as an anticancer strategy. *Expert Opin Ther Tar* 2009, 13 (4), 469-478; and Powers, M. V.; Workman, P., Inhibitors of the heat shock response: Biology and pharmacology. *Febs Lett* 2007, 581 (19), 3758-3769;

the entire contents of which are incorporated herein by reference.

HSF1 and other heat shock proteins (whose expression is increased by HSF1) are over-expressed in, or have otherwise been implicated in, breast, endometrial, fibrosarcoma, gastric, kidney, liver, lung, lymphoma, neuroectodermal, neuroblastoma, Ewing's sarcoma, prostate, skin, squamous cell, and testicular cancers, leukemia (e.g. promyelocytic leukemia), head and neck cancer, and Hodgkin's disease.

In yet another aspect, the present invention provides a compound of formula (I) as defined herein, or a pharmaceutically acceptable salt or solvate thereof, for use in the treatment of a proliferative disorder.

In yet another aspect, the present invention provides the use of a compound of formula (I) as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplastic growth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their HSF1 inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

In one embodiment, the patient or subject in need is a human.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery, radiotherapy or therapy with a chemotherapeutic agent or a molecularly targeted agent. Such additional therapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy)quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) HSP90 inhibitors (for example, geldanamycin, radicicol or 17-N-Allylamino-17-demethoxygeldanamycin (17AAG));

(ix) antisense therapies, for example those which are directed to the targets listed above, such as ISIS 2503, an anti-ras antisense;

(x) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (xi) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

It is anticipated that the HSF1 inhibitors of the present invention are particularly suited to combination therapy with anti-tumour agents that inhibit HSP90 (for example, geldanamycin, radicicol or 17-N-Allylamino-17-demethoxygeldanamycin (17AAG)).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(xi) above.

In a further aspect of the invention there is provided a compound of the invention or a pharmaceutically acceptable salt or solvate thereof, in combination with an anti-tumour agent selected from one listed under (i)-(xi) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(xi) herein above, in association with a pharmaceutically acceptable diluent or carrier.

In another aspect, the compounds of the present invention may be used for the treatment of other HSF1-mediated diseases or conditions, such as autoimmune and viral diseases. In the case of autoimmune diseases, the compounds of the invention may be combined with other agents for the treatment of autoimmune conditions, for example, steroids and other immunosuppressant agents. In the case of viral diseases, the compounds of the invention may be administered with one or more additional antiviral agents.

EXAMPLES

Chemistry

Unless otherwise stated, reactions were conducted in oven dried glassware under an atmosphere of nitrogen or argon using anhydrous solvents. All commercially obtained reagents and solvents were used as received.

Thin layer chromatography (TLC) was performed on pre-coated aluminium sheets of silica (60 F254 nm, Merck) and visualized using short-wave UV light. Flash column chromatography was carried out on Merck silica gel 60 (partial size 40-65 μm). Column chromatography was also performed on a Biotage SP1 purification system using Biotage Flash silica cartridges (SNAP KP-Sil). Ion exchange chromatography was performed using acidic Isolute Flash SCX-II columns.

$^1$H-NMR spectra were recorded on Bruker AMX500 (500 MHz) spectrometers using an internal deuterium lock. Chemical shifts are quoted in parts per million (ppm) using the following internal references: CDCl$_3$ (δH 7.26), MeOD (δH 3.31) and DMSO-d$_6$ (δH 2.50). Signal multiplicities are recorded as singlet (s), doublet (d), triplet (t), quartet (q) and multiplet (m), doublet of doublets (dd), doublet of doublet of doublets (ddd), apparent (app), broad (br) or obscured (obs). Coupling constants, J, are measured to the nearest 0.1 Hz. $^{13}$C-NMR spectra were recorded on Bruker AMX500 spectrometers at 126 MHz using an internal deuterium lock. Chemical shifts are quoted to 0.01 ppm, unless greater accuracy was required, using the following internal references: CDCl$_3$ (δC 77.0), MeOD (δC 49.0) and DMSO-d$_6$ (δC 39.5).

High resolution mass spectra were recorded on an Agilent 1200 series HPLC and diode array detector coupled to a 6210 time of flight mass spectrometer with dual multimode APCI/ESI source or on a Waters Acquity UPLC and diode array detector coupled to a Waters G2 QToF mass spectrometer fitted with a multimode ESI/APCI source.

Analytical separation was carried out according to the methods listed below. The mobile phase was a mixture of methanol (solvent A) and water (solvent B), both containing formic acid at 0.1%, UV detection was at 254 nm. Method I: Agilent 1200 series HPLC, Merck Purospher STAR (RP-18e, 30×4 mm) column using a flow rate of 1.5 mL/min in a 4 minute gradient elution. Gradient elution was as follows: 10:90 (A/B) to 90:10 (A/B) over 2.5 min, 90:10 (A/B) for 1 min, and then reversion back to 10:90 (A/B) over 0.3 min, finally 10:90 (A/B) for 0.2 min. Method II: Agilent 1200 series HPLC, Merck Chromolith Flash column (RP-18e, 25×2 mm) at 30° C. using a flow rate of 0.75 mL/min in a 4 minute gradient elution. Gradient elution was as follows: 5:95 (A/B) to 100:0 (A/B) over 2.5 min, 100:0 (A/B) for 1 min, and then reversion back to 5:95 (A/B) over 0.1 min, finally 5:95 (A/B) for 0.4 min. Method III: Waters Acquity UPLC, Phenomenex Kinetex XB-C18 column (30×2.1 mm, 1.7u, 100 A) at 30° C. using flow rate of 0.3 mL/min in a 4 minute gradient elution. Gradient elution was as follows: 10:90 (A/B) to 90:10 (A/B) over 3 min, 90:10 (A/B) for 0.5 min, and then reversion back to 10:90 (A/B) over 0.3 min, finally 10:90 (A/B) for 0.2 min; Method IV: Waters Acquity UPLC, Phenomenex Kinetex C18 column (30×2.1 mm, 2.6u, 100 A), flow rate and gradient elution according to Method III.

The following reference masses were used for HRMS analysis: Agilent 1200 series: caffeine [M+H]$^+$ 195.087652; hexakis(1H,1H,3H-tetrafluoropentoxy)phosphazene [M+H]$^+$922.009798 and hexakis(2,2-difluoroethoxy)phosphazene [M+H]$^+$ 622.02896 or reserpine [M+H]$^+$ 609.280657; Waters Acquity UPLC: Leucine Enkephalin fragment ion [M+H]+ 397.1876. All compounds were >95% purity by LCMS analysis unless otherwise stated.

N-(2-Fluoro-5-nitrophenyl)-2-methylquinoline-6-carboxamide

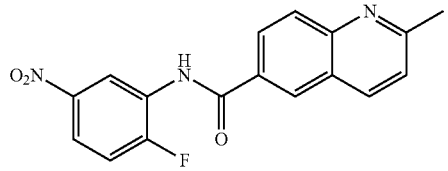 [SMILES: Cc1ccc2cc(C(=O)Nc3cc([N+](=O)[O-])ccc3F)ccc2n1]

In an oven dried 250 mL RBF under an inert atmosphere, oxalyl chloride (3.25 mL, 38.4 mmol) was added dropwise to a solution of 2-methylquinoline-6-carboxylic acid (6.59 g, 35.2 mmol) and DMF (0.0062 mL, 0.080 mmol) in anhydrous dichloromethane (80 mL). The reaction mixture was stirred at room temperature for 3 h, and then concentrated under reduced pressure. The residue was dissolved in dichloromethane and concentrated again under reduced pressure. The obtained dry residue was dissolved in pyridine (80 mL) and 2-fluoro-5-nitroaniline (5.00 g, 32.00 mmol) was added in one portion. The reaction mixture was stirred at room temperature for 18 h, and then poured onto water (100 mL). The green precipitate was filtered and washed several times with water, diethyl ether and finally with a minimum amount of dichloromethane to afford the title compound (10.42 g,) as a light green solid which was carried onto the next step as a crude. $^1$H NMR (500 MHz, DMSO-d$_6$) b 10.70 (s, 1H), 8.72 (dd, J=6.45, 2.93 Hz, 1H), 8.63 (d, J=2.02 Hz, 1H), 8.43 (d, J=8.46 Hz, 1H), 8.23 (dd, J=8.48, 2.02 Hz, 1H), 8.21-8.16 (m, 1H), 8.05 (d, J=8.86 Hz, 1H), 7.65 (app t, J=9.25 Hz, 1H), 7.54 (d, J=8.46 Hz, 1H), 2.71 (s, 3H). HRMS (ESI+): Found [M+H]$^+$ 326.0934 C$_{17}$H$_{13}$FN$_3$O$_3$ requires 326.0935.

N-(5-Amino-2-fluorophenyl)-2-methylquinoline-6-carboxamide

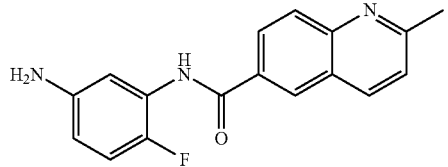

In a 250 mL RBF, to a solution of N-(2-fluoro-5-nitrophenyl)-2-methylquinoline-6-carboxamide (10.42 g, 32.00 mmol) in ethanol (120 mL) and water (40 mL), ammonium chloride (11.99 g, 224 mmol) and iron powder (12.52 g, 224 mmol) were added in one portion and the resulting suspension was allowed to stir at 90° C. for 1 h. The reaction mixture was allowed to cool to room temperature, diluted with MeOH and dichloromethane 1:9 mixture (50 mL) and filtered through a pad of Celite®. The resulting filtrate was concentrated under vacuum to afford a light brown solid which was re-dissolved in a mixture dichloromethane/MeOH 9:1 (150 mL) and washed with NaHCO$_3$ saturated aqueous solution (150 mL). The organic phase was dried over Na$_2$SO$_4$, filtered and concentrated under reduced pressure to afford a yellow solid as crude product, which was carried onto the next step without purification (9.46 g,). $^1$H-NMR (500 MHz, DMSO-d$_6$) δ 10.05 (s, 1H), 8.57 (d, J=1.67 Hz, 1H), 8.39 (d, J=8.74 Hz, 1H), 8.19 (dd, J=8.74, 1.67 Hz, 1H), 8.01 (d, J=8.74 Hz, 1H), 7.52 (d, J=8.33 Hz, 1H), 6.94 (dd, J=9.78, 8.28 Hz, 1H), 6.89 (dd, J=6.58, 2.74 Hz, 1H), 6.46-6.39 (m, 1H), 5.05 (bs, 2H), 2.70 (s, 3H). HRMS (ESI+): Found [M+H]+ 296.1191 C$_{17}$H$_{15}$FN$_3$O requires 296.1194.

N-(5-(2,3-Dihydrobenzo[b][1,4]dioxine-6-carboxamido)-2-fluorophenyl)-2-methylquinoline-6-carboxamide

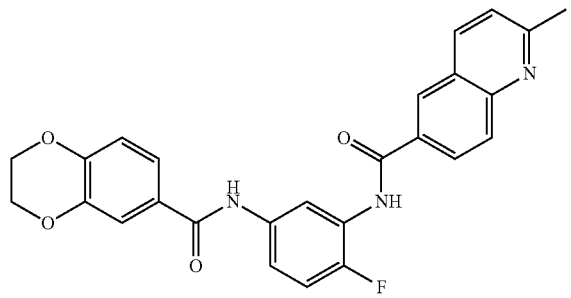 [SMILES: Cc1ccc2cc(C(=O)Nc3cc(NC(=O)c4ccc5c(c4)OCCO5)ccc3F)ccc2n1]

In an oven dried 250 mL RBF under inert atmosphere, to a suspension of 2,3-dihydrobenzo[b][1,4]dioxine-6-carboxylic acid (12.70 g, 70.5 mmol) in anhydrous dichloromethane (100 mL), a catalytic amount of dry DMF (6.16 µl, 0.080 mmol) and oxalyl chloride (6.51 mL, 77 mmol) were added dropwise and the resulting green solution was allowed to stir at room temperature for 3 h after which the reaction mixture was concentrated under vacuum to afford a dry pale green solid. The solid was dissolved in pyridine (100 mL) and N-(5-amino-2-fluorophenyl)-2-methylquinoline-6-carboxamide (9.46 g, 32.0 mmol) was added in one portion. The resulting dark yellow suspension was allowed to stir for 2 h after which it was poured onto water (100 mL). The yellow precipitate was filtered and washed several times with water, diethyl ether and finally with a minimum amount of dichloromethane to afford the crude product as a pale yellow solid which does not require further purification (12.5 g). $^1$H-NMR (500 MHz, DMSO-$d_6$): 10.37 (s, 1H), 10.18 (s, 1H), 8.62 (d, J=1.65 Hz, 1H), 8.41 (d, J=8.77 Hz, 1H), 8.23 (dd, J=8.77, 2.19 Hz, 1H), 8.13 (dd, J=7.01, 2.63 Hz, 1H), 8.03 (d, J=8.51 Hz, 1H), 7.68-7.63 (m, 1H), 7.55-7.53 (m, 2H), 7.52 (dd, J=8.51, 2.09 Hz, 1H), 7.29 (dd, J=9.98, 8.69 Hz, 1H), 6.99 (d, J=8.51 Hz, 1H), 4.34-4.28 (m, 4H), 2.71 (s, 3H). HRMS (ESI+): Found [M+H]$^+$ 459.1520 $C_{26}H_{21}FN_3O_4$ requires 459.1542.

N-(5-(2,3-Dihydrobenzo[b][1,4]dioxine-6-carboxamido)-2-fluorophenyl)-2-formylquinoline-6-carboxamide

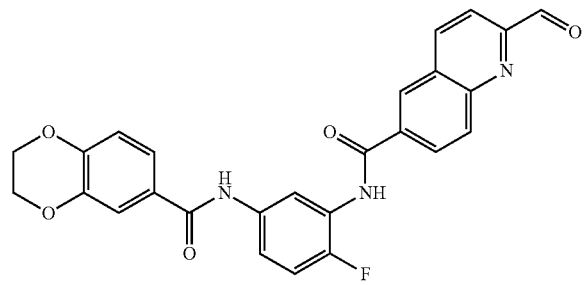 [SMILES: O=Cc1ccc2cc(C(=O)Nc3cc(NC(=O)c4ccc5c(c4)OCCO5)ccc3F)ccc2n1]

In an oven dried 250 mL RBF under inert atmosphere, a solution of N-(5-(2,3-dihydrobenzo[b][1,4]dioxine-6-carboxamido)-2-fluorophenyl)-2-methylquinoline-6-carboxamide (5.00 g, 10.93 mmol) and selenium dioxide (1.334 g, 12.02 mmol) in anhydrous DMF (40.00 mL) and 1,4-dioxane (120.00 mL) was heated at reflux for 1 h after which the reaction mixture was allowed to cool to room temperature, diluted with dichloromethane (100 mL) and filtered through a pad of Celite®. The filtrate was concentrated under vacuum (using an azeotrope of heptane/ethyl acetate in order to remove DMF) to afford the crude product as a yellow solid, which was carried onto the next step without any further purification (5.15 g,). $^1$H-NMR (500 MHz, DMSO-$d_6$): δ 10.54 (s, 1H), 10.19 (s, 1H), 10.17 (s, 1H), 8.81-8.77 (m, 2H), 8.39 (dd, J=8.73, 1.95 Hz, 1H), 8.36 (d, J=8.73 Hz, 1H), 8.17 (dd, J=6.93, 2.57 Hz, 1H), 8.09 (d, J=9.26 Hz, 1H), 7.69-7.64 (m, 1H), 7.55 (d, J=1.99 Hz, 1H), 7.52 (dd, J=8.30, 1.99 Hz, 1H), 7.31 (app t, J=9.97 Hz, 1H), 6.99 (d, J=8.30 Hz, 1H), 4.36-4.27 (m, 4H). HRMS (ESI+): Found [M+H]$^+$ 472.1286 $C_{26}H_{19}FN_3O_5$ requires 472.1303.

tert-Butyl 4-ethyl-$d_5$-piperazine-1-carboxylate

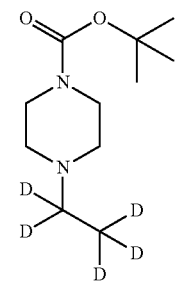 [SMILES: [2H]C([2H])([2H])C([2H])([2H])N1CCN(C(=O)OC(C)(C)C)CC1]

tert-Butyl piperazine-1-carboxylate (538 mg, 2.89 mmol) and NaHCO$_3$ (364 mg, 4.33 mmol) were suspended in anhydrous THF (25 mL) under inert atmosphere. The resulting mixture was cooled to 0° C., then iodoethane-$d_5$ (0.231 mL, 2.89 mmol) was added dropwise and the reaction mixture was allowed to stir at 50° C. After 2 h the heating was removed and the reaction mixture was allowed to stir at 20° C. overnight. The solvent was removed under reduced pressure to afford a white solid, which was re-dissolved in dichloromethane/MeOH 9:1 mixture (20 mL) and washed with NaHCO$_3$ saturated aqueous solution (20 mL). The aqueous phase was extracted with dichloromethane/MeOH 9:1 mixture (3×20 mL). The organic layers were combined, dried over MgSO$_4$, filtered and concentrated under reduced pressure to afford a yellow thick oil as crude product. The crude was purified by column chromatography on silica gel in gradient dichloromethane/MeOH 0-1%, to afford the title compound (0.33 g, 52%) as a pale yellow oil. $^1$H NMR (500 MHz, Chloroform-d) δ 3.32-3.23 (m, 4H), 2.66 (t, J=5.1 Hz, 2H), 2.22 (t, J=5.0 Hz, 2H), 1.26 (s, 9H). HRMS (ESI+): Found [M+Na]$^+$242.1889 $C_{11}H_{17}D_5N_2NaO_2$ requires 242.1887.

1-Ethyl-$d_5$-piperazine

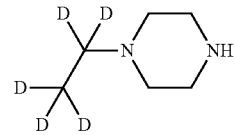 [SMILES: [2H]C([2H])([2H])C([2H])([2H])N1CCNCC1]

tert-Butyl 4-ethyl-$d_5$-piperazine-1-carboxylate (0.327 g, 1.491 mmol) was dissolved in anhydrous dichloromethane (10 mL) and HCl 4.0 M in 1,4-dioxane (5.59 mL, 22.36 mmol) was added dropwise. The reaction mixture was allowed to stir at 20° C. for 24 h and then it was concentrated under reduced pressure to afford a white solid as crude product, which was carried onto the next step without purification. H NMR (500 MHz, DMSO-$d_6$) b 3.84-3.19 (m, 8H). LCMS (ESI+): RT 0.15 min, m/z 120.1590 [M+H]+.

N-(5-(2,3-Dihydrobenzo[b][1,4]dioxine-6-carboxamido)-2-fluorophenyl)-2-((4-ethyl-d$_5$-piperazin-1-yl)methyl)quinoline-6-carboxamide (Compound A)

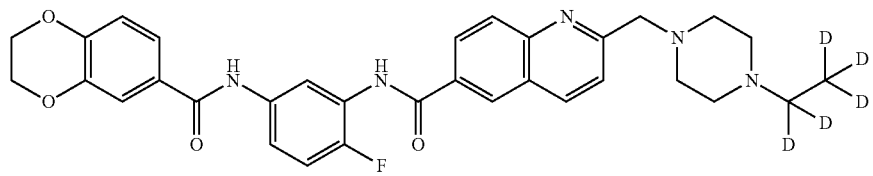 [SMILES: [2H]C([2H])([2H])C([2H])([2H])N1CCN(Cc2ccc3cc(C(=O)Nc4cc(NC(=O)c5ccc6c(c5)OCCO6)ccc4F)ccc3n2)CC1]

N-(5-(2,3-Dihydrobenzo[b][1,4]dioxine-6-carboxamido)-2-fluorophenyl)-2-formylquinoline-6-carboxamide (235 mg, 0.498 mmol) and compound 1-ethyl-d$_5$-piperazine (178 mg, 1.493 mmol) were suspended in anhydrous dichloromethane (7 mL) and the resulting red suspension was allowed to stir at 20° C. for 20 h. Then sodium triacetoxyborohydride (316 mg, 1.493 mmol) was added in one portion and the resulting mixture was allowed to stir for 1 h. The reaction mixture was diluted with dichloromethane (5 mL) and washed with NaHCO$_3$ saturated aqueous solution (10 mL). The aqueous phase was extracted with dichloromethane/MeOH 9:1 mixture (3×10 mL). The organic layers were combined, dried over Na$_2$SO$_4$, filtered and concentrated under reduced pressure to afford a brown solid as crude product. Purification by column chromatography on silica gel in gradient dichloromethane/MeOH 0-7.5%, followed by trituration in diethyl ether and ethyl acetate afforded the title compound as a light beige solid (0.06 g, 21%). $^1$H NMR (500 MHz, DMSO-d$_6$) b 10.40 (s, 1H), 10.19 (s, 1H), 8.65 (d, J=2.1 Hz, 1H), 8.49 (d, J=8.6 Hz, 1H), 8.25 (dd, J=8.8, 2.1 Hz, 1H), 8.17-8.05 (m, 2H), 7.73 (d, J=8.5 Hz, 1H), 7.66 (dt, J=8.9, 3.4 Hz, 1H), 7.57-7.49 (m, 2H), 7.29 (t, J=9.5 Hz, 1H), 6.99 (d, J=8.4 Hz, 1H), 4.31 (td, J=5.1, 3.3 Hz, 4H), 3.79 (s, 2H), 2.50 (s, 8H). HRMS (ESI+): Found [M+H]+ 575.2821 C$_{32}$H$_{28}$D$_5$FN$_5$O$_4$ requires 575.2825.

tert-Butyl 4-ethylpiperazine-d$_5$-1-carboxylate

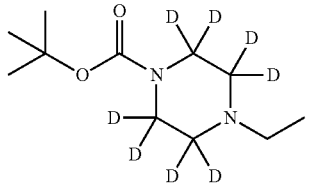 [SMILES: [2H]C1([2H])N(CC)C([2H])([2H])C([2H])([2H])N(C(=O)OC(C)(C)C)C1([2H])[2H]]

To a solution of tert-butyl piperazine-d$_8$-1-carboxylate (154 mg, 0.793 mmol) in anhydrous MeOH (10 mL), sodium cyanoborohydride (158 mg, 3.96 mmol) was added in one portion. The resulting mixture was cooled to 0° C. and acetaldehyde (0.031 mL, 0.555 mmol) was added slowly and dropwise. The resulting clear pale yellow solution was allowed to stir at 20° C. for 3 h. The reaction mixture was concentrated under reduced pressure, then re-dissolved in dichloromethane/MeOH 9:1 mixture (10 mL), and washed with NaOH (1N) aqueous solution (10 mL). The aqueous phase was extracted with dichloromethane/MeOH 9:1 mixture (3×10 mL). The organic layers were combined, dried over MgSO$_4$, filtered and concentrated under reduced pressure to afford the crude product as a glassy colourless solid. Purification by column chromatography on a short pad of silica in isocratic elution with CHCl$_3$/MeOH 9:1 mixture afforded the title compound as a colourless thick oil (0.04 g, 23%). $^1$H NMR (500 MHz, Methanol-d$_4$) δ 2.46 (q, J=7.3 Hz, 2H), 1.47 (s, 9H), 1.12 (t, J=7.2 Hz, 3H). LCMS (ESI+): RT 0.37 min, m/z 223.2276 [M+H]+.

1-Ethyl-piperazine-d$_8$

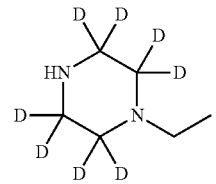 [SMILES: [2H]C1([2H])NC([2H])([2H])C([2H])([2H])N(CC)C1([2H])[2H]]

tert-Butyl 4-ethylpiperazine-d$_8$-1-carboxylate (39 mg, 0.175 mmol) was dissolved in anhydrous MeOH (1.5 mL) then HCl 4.0 M in 1,4-dioxane (0.658 mL, 2.63 mmol) was added dropwise and the resulting clear pale yellow solution was allowed to stir at 20° C. for 2 h. Then the reaction mixture was concentrated under reduced pressure to afford a light beige solid as crude product, which was carried onto the next step without purification. LCMS (ESI+): RT 0.15 min, m/z 123.1777 [M+H]+.

N-(5-(2,3-Dihydrobenzo[b][1,4]dioxine-6-carboxamido)-2-fluorophenyl)-2-((4-ethyl-piperazin-d$_8$-1-yl)methyl)quinoline-6-carboxamide (Compound B)

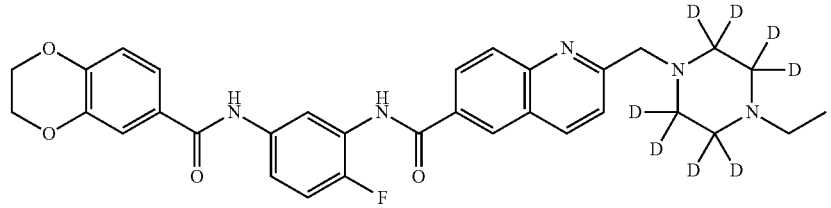 [SMILES: [2H]C1([2H])N(CC)C([2H])([2H])C([2H])([2H])N(Cc2ccc3cc(C(=O)Nc4cc(NC(=O)c5ccc6c(c5)OCCO6)ccc4F)ccc3n2)C1([2H])[2H]]

N-(5-(2,3-Dihydrobenzo[b][1,4]dioxine-6-carboxamido)-2-fluorophenyl)-2-formylquinoline-6-carboxamide (27.0 mg, 0.057 mmol) and 1-ethyl-piperazine-d$_8$ (21 mg, 0.172 mmol) were suspended in anhydrous MeOH (1.0 mL) and the resulting red suspension was allowed to stir at 20° C. for 20 h. Then sodium cyanoborohydride (10.80 mg, 0.172 mmol) was added in one portion and the resulting mixture was allowed to stir for 1 h. The reaction mixture was concentrated under reduced pressure, re-dissolved in dichloromethane/MeOH 9:1 mixture (5 mL) and washed with NaOH (1N) aqueous solution (5 mL). The aqueous phase was extracted with dichloromethane/MeOH 9:1 mixture (3×5 mL). The organic layers were combined, dried over $Na_2SO_4$, filtered and concentrated under reduced pressure to afford a light brown solid as crude product. Purification by column chromatography on silica gel in gradient dichloromethane/MeOH 0-10% afforded the title compound as a white solid (1.59 mg, 32%). $^1$H NMR (500 MHz, Methanol-$d_4$) δ 8.77-8.63 (bs, 2H), 8.40 (dd, J=8.8, 2.0 Hz, 1H), 8.30-8.20 (m, 2H), 7.91 (d, J=8.6 Hz, 1H), 7.58 (ddd, J=8.9, 4.3, 2.7 Hz, 1H), 7.55-7.46 (m, 2H), 7.26 (dd, J=10.1, 9.0 Hz, 1H), 6.97 (d, J=8.3 Hz, 1H), 4.36-4.31 (m, 4H), 4.21 (s, 2H), 3.28 (q, J=7.4 Hz, 2H), 1.39 (t, J=7.3 Hz, 3H). HRMS (ESI+): Found [M+H]$^+$ 578.2957 $C_{32}H_{25}D_8FN_5O_4$ requires 578.3013.

2-((tert-Butyldimethylsilyl)oxy)ethanol-$d_4$

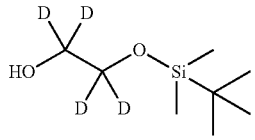

To a stirred solution of ethylene-$d_4$ glycol (1.0 g, 15.13 mmol) and triethylamine (1.093 mL, 15.13 mmol) in anhydrous dichloromethane (20 mL) at 0° C. a solution of tert-butylchlorodimethylsilane (1.14 g, 7.57 mmol) in anhydrous dichloromethane (12 mL) was added dropwise and the resulting mixture was allowed to warm to room temperature and stir for 16 h. The reaction was quenched with NaHCO$_3$ saturated aqueous solution (20 mL) and the layers were separated. The aqueous layer was extracted with dichloromethane (3×20 mL) and the combined organic layers were dried over MgSO$_4$, filtered and concentrated in vacuo. Purification by flash column chromatography (0-50% EtOAc in cyclohexane) afforded the title compound as a colourless oil (2.62 g, 96%). $^1$H NMR (500 MHz, Chloroform-d) δ 0.86 (s, 9H), 0.04 (s, 6H). HRMS (ESI+): Found [M+H]$^+$ 182.1584 $C_8H_{17}D_4O_2Si$ requires 182.1577.

Methyl 3-(2-((tert-butyldimethylsilyl)oxy)eth-$d_4$-oxy)-4-hydroxybenzoate

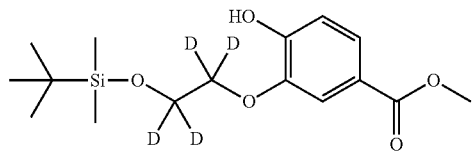 [SMILES: [2H]C([2H])(Oc1cc(C(=O)OC)ccc1O)C([2H])([2H])O[Si](C)(C)C(C)(C)C]

DIAD (0.434 mL, 2.230 mmol) was added to a stirred solution of 2-((tert-butyldimethylsilyl)oxy)ethanol-$d_4$ (322 mg, 1.784 mmol), methyl 3,4-dihydroxybenzoate (250 mg, 1.487 mmol) and triphenylphosphine (585 mg, 2.230 mmol) in anhydrous THF (10 mL) at room temperature. The reaction was allowed to stir for 16 h at room temperature. The reaction was quenched with water (20 mL) and diluted with ethyl acetate (40 mL) and the layers were separated. The aqueous layer was washed with ethyl acetate (3×40 mL) and the combined organic layers were dried over MgSO4, filtered and concentrated in vacuo. Purification by flash column chromatography (0-10% Cyclohexane-Ethyl acetate) afforded the title compound as a colourless oil (482 mg, 98%). $^1$H NMR (500 MHz, Chloroform-d) δ 7.61 (d, J=2.1 Hz, 1H), 7.59-7.54 (m, 2H), 3.84 (s, 3H), 0.93 (s, 9H), 0.12 (s, 6H) (mixture of regioisomers, major product reported). HRMS (ESI+): Found [M+H]$^+$ 333.1889 $C_{16}H_{23}D_4O_5Si$ requires 333.1883.

Methyl 4-hydroxy-3-(2-hydroxyeth-$d_4$-oxy)benzoate

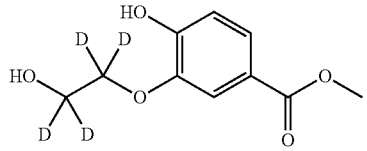 [SMILES: [2H]C([2H])(O)C([2H])([2H])Oc1cc(C(=O)OC)ccc1O]

TBAF (0.363 mL, 0.363 mmol) was added to a stirred solution of methyl 3-(2-((tert-butyldimethylsilyl)oxy)eth-$d_4$-oxy)-4-hydroxybenzoate (80 mg, 0.242 mmol) in anhydrous THF (10 mL) at room temperature for 1 h. The reaction mixture was quenched with NH$_4$Cl saturated aqueous solution (10 mL) and diluted with ethyl acetate (10 mL). The layers were separated. The aqueous layer was extracted with ethyl acetate (3×10 mL) and the combined organic layers were dried over MgSO4, filtered and concentrated in vacuo. Purification by flash column chromatography (0-50% Cyclohexane-Ethyl acetate) afforded the title compound (47 mg, 90%). $^1$H NMR (500 MHz, Chloroform-d) δ 7.64-7.57 (m, 2H), 6.90 (d, J=8.3 Hz, 1H), 3.90 (s, 3H). HRMS (ESI+): Found [M+H]$^+$ 218.1048 $C_{10}H_9D_4O_5$ requires 218.1043.

Methyl 2,3-dihydrobenzo-$d_4$-[b][1,4]dioxine-6-carboxylate

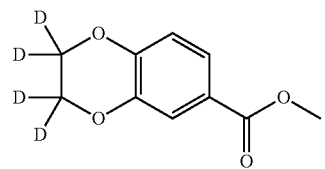 [SMILES: [2H]C1([2H])Oc2ccc(C(=O)OC)cc2OC1([2H])[2H]]

DIAD (0.081 mL, 0.416 mmol) was added to a stirred solution of methyl 4-hydroxy-3-(2-hydroxyeth-$d_4$-oxy)benzoate (60 mg, 0.277 mmol) and triphenylphosphine (109 mg, 0.416 mmol) in anhydrous THF (6 mL) at room temperature and the resulting mixture was allowed to stir for 16 h. The reaction mixture was quenched with water (20 mL) and diluted with ethyl acetate (40 mL) and the layers were separated. The aqueous layer was washed with ethyl acetate (3×40 mL) and the combined organic layers were dried over MgSO4, filtered and concentrated in vacuo. Purification by flash column chromatography (0-10% Cyclohexane-Ethyl acetate) afforded the title compound as a white solid (52 mg, 95%). $^1$H NMR (500 MHz, Chloroform-d) δ 8.39 (d, J=2.0 Hz, 1H), 7.95 (dd, J=8.5, 2.0 Hz, 1H), 7.02 (d, J=8.5 Hz, 1H), 3.91 (s, 3H). HRMS (ESI+): Found [M+H]+ 199.0917 $C_{10}H_7D_4O_4$ requires 199.0903.

2,3-Dihydrobenzo-d₄-[b][1,4]dioxine-6-carboxylic acid

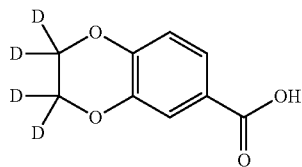 [SMILES: [2H]C1([2H])Oc2ccc(C(=O)O)cc2OC1([2H])[2H]]

Sodium hydroxide (60.5 mg, 1.514 mmol) was added to a stirred solution of methyl 2,3-dihydrobenzo-d₄-[b][1,4]dioxine-6-carboxylate (60 mg, 0.303 mmol) in MeOH (3.00 mL) and water (3 mL) at room temperature. The reaction was allowed to stir overnight and then concentrated in vacuo to remove MeOH. The mixture was acidified to pH 1 using 1 M aqueous solution of HCl and diluted with water (7 mL) and ethyl acetate. The layers were separated and the aqueous layer was extracted with ethyl acetate (10 mL). The combined organic layers were dried over MgSO4, filtered and concentrated in vacuo. The product was obtained as an off-white solid and it was carried onto the next step without purification (32 mg, 57%). $^1$H NMR (500 MHz, DMSO-$d_6$) δ 12.67 (s, 1H), 7.55-7.29 (m, 2H), 6.94 (d, J=8.4 Hz, 1H). HRMS (ESI+): Found [M+H]$^+$ 185.0757 $C_9H_5D_4O_4$ requires 185.0746.

N-(5-(2,3-Dihydrobenzo-d₄-[b][1,4]dioxine-6-carboxamido)-2-fluorophenyl)-2-formylquinoline-6-carboxamide

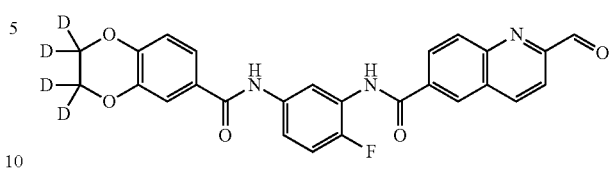

A suspension of N-(5-(2,3-dihydrobenzo-d₄-[b][1,4]dioxine-6-carboxamido)-2-fluorophenyl)-2-methylquinoline-6-carboxamide (34.9 mg, 0.076 mmol) and SeO₂ (9.23 mg, 0.083 mmol) in anhydrous DMF (0.2 mL) and anhydrous 1,4-dioxane (0.9 mL) was heated at reflux. After 1 h the reaction mixture was allowed to cool to room temperature, it was diluted with dichloromethane and filtered through a pad of Celite®. The filtrate was concentrated under reduced pressure to afford the crude product as a yellow solid, which was carried onto the next step without further purification. HRMS (ESI+): Found [M+H]+ 476.1516 $C_{26}H_{15}D_4FN_3O_5$ requires 476.1554.

N-(5-(2,3-Dihydrobenzo-d₄-[b][1,4]dioxine-6-carboxamido)-2-fluorophenyl)-2-((4-ethylpiperazin-1-yl)methyl)quinoline-6-carboxamide (Compound C)

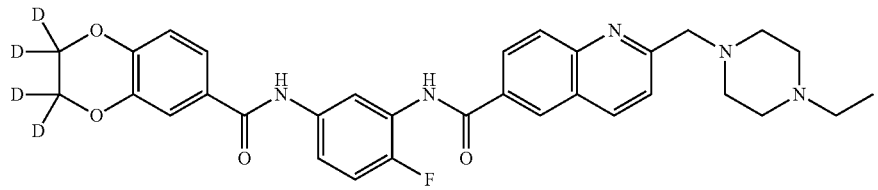

N-(5-(2,3-Dihydrobenzo-d₄-[b][1,4]dioxine-6-carboxamido)-2-fluorophenyl)-2-methylquinoline-6-carboxamide

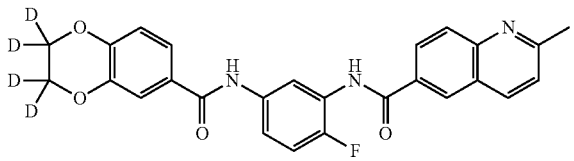 [SMILES: [2H]C1([2H])Oc2ccc(C(=O)Nc3ccc(F)c(NC(=O)c4ccc5nc(C)ccc5c4)c3)cc2OC1([2H])[2H]]

N-(5-amino-2-fluorophenyl)-2-methylquinoline-6-carboxamide (40.1 mg, 0.136 mmol), 2,3-dihydrobenzo-d₄-[b][1,4]dioxine-6-carboxylic acid (30.0 mg, 0.163 mmol) and HATU (77 mg, 0.204 mmol) were dissolved in anhydrous DMF (1.0 mL) then DIPEA (0.071 mL, 0.407 mmol) was added dropwise and the resulting brown solution was allowed to stir at 20° C. for 20 h. The reaction mixture was poured onto water and the resulting yellow precipitate was washed several times with water. The crude product was purified by column chromatography in gradient dichloromethane/MeOH 0-10% to afford the title compound as a pale yellow solid (39 mg, 62%). $^1$H NMR (500 MHz, DMSO-$d_6$) δ 10.37 (s, 1H), 10.18 (s, 1H), 8.62 (d, J=2.0 Hz, 1H), 8.44-8.38 (m, 1H), 8.23 (dd, J=8.7, 2.1 Hz, 1H), 8.13 (dd, J=7.1, 2.7 Hz, 1H), 8.03 (d, J=8.8 Hz, 1H), 7.65 (ddd, J=9.1, 4.3, 2.7 Hz, 1H), 7.56-7.48 (m, 3H), 7.29 (dd, J=10.1, 9.0 Hz, 1H), 6.99 (d, J=8.4 Hz, 1H), 2.71 (s, 3H). HRMS (ESI+): Found [M+H]+ 462.1744 $C_{26}H_{17}D_4FN_3O_4$ requires 462.1762.

N-(5-(2,3-Dihydrobenzo-d₄-[b][1,4]dioxine-6-carboxamido)-2-fluorophenyl)-2-formylquinoline-6-carboxamide (36 mg, 0.076 mmol) and 1-ethylpiperazine (0.029 mL, 0.227 mmol) were suspended in anhydrous dichloromethane (1.0 mL) and the resulting red suspension was allowed to stir at 20° C. for 20 h. Then sodium triacetoxyborohydride (48.1 mg, 0.227 mmol) was added in one portion and the resulting mixture was allowed to stir for 24 h. The reaction was diluted with dichloromethane (1 mL) and washed with NaHCO₃ saturated aqueous solution (2 mL). The aqueous phase was extracted with dichloromethane/MeOH 9:1 mixture (3×5 mL) and the organic layers were collected, dried over Na₂SO₄, filtered and concentrated under reduced pressure to afford a dark orange thick oil as crude product. The crude product was purified by column chromatography in gradient dichloromethane/MeOH 0-10%, followed by purification by Isolute SCX-II column in dichloromethane/MeOH/NH₃ to afford the title compound as a white solid (11.4 mg, 26%). $^1$H NMR (500 MHz, DMSO-$d_6$) δ 10.39 (s, 1H), 10.18 (s, 1H), 8.65 (d, J=1.7 Hz, 1H), 8.49 (d, J=8.6 Hz, 1H), 8.25 (dd, J=8.8, 1.9 Hz, 1H), 8.21-8.02 (m, 2H), 7.78-7.62 (m, 2H), 7.61-7.43 (m, 2H), 7.29 (t, J=9.5 Hz, 1H), 6.99 (d, J=8.4 Hz, 1H), 3.81 (s, 2H), 2.70-2.35 (m, 10H), 1.03 (s, 3H). HRMS (ESI+): Found [M+H]$^+$ 575.2773 $C_{32}H_{29}D_4FN_5O_4$ requires 575.2793.

N-(5-(2,3-Dihydrobenzo[b][1,4]dioxine-6-carboxamido)-2-fluorophenyl)-2-((4-ethylpiperazin-1-yl)methyl)quinoline-6-carboxamide (Reference Compound D)

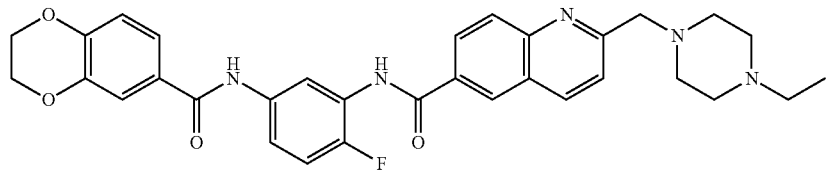 [SMILES: CCN1CCN(Cc2ccc3cc(C(=O)Nc4cc(NC(=O)c5ccc6c(c5)OCCO6)ccc4F)ccc3n2)CC1]

A solution of N-(5-(2,3-Dihydrobenzo[b][1,4]dioxine-6-carboxamido)-2-fluorophenyl)-2-formylquinoline-6-carboxamide (1.19 g, 2.52 mmol) and 1-ethylpiperazine in anhydrous dichloromethane (20 mL) was allowed to stir at 20° C. for 6 h, after which sodium triacetoxyborohydride (1.605 g, 7.57 mmol) was added in one portion and the resulting mixture was allowed to stir at 20° C. for 2 h. The reaction was quenched with NaHCO$_3$ aqueous saturated solution (20 mL) and extracted with a mixture dichloromethane/MeOH 9/1 (3×20 mL). Purification by column chromatography on silica gel in gradient (dichloromethane/MeOH) afforded a yellow solid, which was re-dissolved in dichloromethane/MeOH 9:1 mixture (100 mL) and washed with water (100 mL). The organic phase was dried over Na$_2$SO$_4$, filtered and concentrated under reduced pressure. Final trituration in diethyl ether afforded the desired product as a white solid (0.950 g, 66%). $^1$H-NMR (500 MHz, DMSO-d$_6$): δ10.41 (s, 1H), 10.20 (s, 1H), 8.66 (d, J=1.86 Hz, 1H), 8.49 (d, J=8.67 Hz, 1H), 8.26 (dd, J=8.67, 1.86 Hz, 1H), 8.14 (dd, J=7.14, 2.55 Hz, 1H), 8.08 (d, J=8.67 Hz, 1H), 7.73 (d, J=8.27 Hz, 1H), 7.69-7.62 (m, 1H), 7.55 (d, J=1.83 Hz, 1H), 7.53 (dd, J=8.53, 1.83 Hz, 1H), 7.29 (app t, J=9.16 Hz, 1H), 6.99 (d, J=8.53 Hz, 1H), 4.36-4.25 (m, 4H), 3.79 (s, 2H), 2.64-2.18 (m, 10H), 0.99 (t, J=6.41 Hz, 3H). HRMS (ESI+): Found [M+H]$^+$ 571.2527 C$_{32}$H$_{33}$FN$_5$O$_4$ requires 571.2542.

Biology

Cell line: The human ovarian carcinoma cell line (SK-OV-3) was obtained from an ICR collaborator in the 1990s. Prior to use, the cells were analyzed by short tandem repeat (STR) profiling. Polymorphic STR loci were amplified using a polymerase chain reaction (PCR) primer set. The PCR product (each locus being labelled with a different fluorophore) was analyzed simultaneously with size standards using automated fluorescent detection. The number of repeats at 10 different loci (as recommended by the American Type Culture Collection, ATCC) was used to define the STR profile and this was cross-referenced with online databases to confirm authenticity. Using this method, the in vivo subline showed an acceptable 85.71% identity with the ATCC reference line (LGC Promochem, UK). The cells were free of mycoplasma contamination as determined by a sensitive nested PCR protocol (Venor GeM kit, Minerva Biolabs, Germany). Cells were grown in DMEM/10% FCS, 2 mM glutamine and nonessential amino acids in 5% CO$_2$.

Cell-Based ELISA (Cellisa) for HSP72 Expression

To follow HSP72 protein expression, a product of HSF1 transcriptional activity, the Cellisa was developed. Cells (5-8×10$^4$ cells/mL) were seeded into 96-well plates and incubated at 37° C. for 48 h. Compounds were then added at a range of concentrations and incubated for 1 h before addition of 17-AAG (250 nM). Cells were then incubated for 18 h. The medium was removed and cells were fixed with fixing solution (4% paraformaldehyde, 0.3% TritonX-100 in PBS buffer) for 30 min at 4° C. The plates were then washed with 0.1% Tween-20/deionized water, before blocking with 5% milk for 30 mins at 37° C. After washing the plates, HSP72 antibody (SPA-810, Enzo Life) was added for 1.5 h at 37° C. Following 4× washes, the plates were incubated with europium-labelled anti-mouse antibody (0.6 µg/mL) in Delfia assay buffer (Perkin Elmer) for 1 h at 37° C. After washing the plates, Delfia enhancement solution was added, shaken for 10 min before reading in the Envision plate reader (Perkin-Elmer) with excitation at 340 nm and emission at 615 nm. The plates were washed again before total protein determination using the Pierce BCA assay (Thermo Scientific) following the manufacturers standard protocol. The europium counts were normalized for the amount of protein in each well. The 50% inhibitory concentration (IC$_{50}$) of the compound was determined by fitting the data to a dose-response curve without limits using non-linear regression. Each concentration was tested once.

In Vitro Cell Viability Assay

The cell titer blue viability (CTB) (Promega) assay provides a homogenous, fluorometric method for estimating the number of viable cells. It uses the dark blue indicator dye resazurin to measure the metabolic capacity of cells which is an indicator of cell viability. Viable cells are able to reduce resazurin into resorufin (pink), which is highly fluorescent. Briefly, cells (~6×10$^3$ cells/mL) were seeded into 384-well plates and were incubated for 24 h. Compounds (at a range of concentrations) were added using the ECHO 550 liquid handler (Labcyte, USA) and then left at 37° C. for 96 h. Titre blue reagent was added to each well and left at 37° C. for 3-4 h. Fluorescence was measured using the Envision machine (Perkin Elmer, UK). The 50% growth inhibitory concentration (GI$_{50}$) was determined by fitting the data to a dose-response curve without limits using non-linear regression. Each concentration was tested twice.

In Vitro Hepatocyte Stability Assay (Cyprotex)

Protocol Summary

Test compound (1 µM) is incubated with cryopreserved hepatocytes in suspension. Samples are removed at 6 time points over the course of a 60 min experiment and test compound is analysed by LC-MS/MS. An intrinsic clearance value (CL$_{int}$) with standard error and half-life (t$_{1/2}$) is delivered.

Objective

To determine the stability of the test compound in the presence of cryopreserved hepatocytes.

Experimental Procedure

Cryopreserved pooled hepatocytes are purchased from a reputable commercial supplier. A range of species and strains are available upon request. Cryopreserved hepatocytes are stored in liquid nitrogen prior to use.

Williams E media supplemented with 2 mM L-glutamine and 25 mM HEPES and test compound (final substrate concentration 1 µM; final DMSO concentration 0.25%) are pre-incubated at 37° C. prior to the addition of a suspension of cryopreserved hepatocytes (final cell density 0.5×10$^6$ viable cells/mL in Williams E media supplemented with 2 mM L-glutamine and 25 mM HEPES) to initiate the reaction. The final incubation volume is 500 µL. Two control compounds are included with each species, alongside appropriate vehicle control.

The reactions are stopped by transferring 50 µL of incubate to 100 µL methanol containing internal standard at the appropriate time points. The termination plates are centrifuged at 2500 rpm at 4° C. for 30 min to precipitate the protein.

Quantitative Analysis

Following protein precipitation, the sample supernatants are combined in cassettes of up to 4 compounds and analysed using Cyprotex generic LC-MS/MS conditions.

Data Analysis

From a plot of ln peak area ratio (compound peak area/internal standard peak area) against time, the gradient of the line is determined. Subsequently, half-life ($t_{1/2}$) and intrinsic clearance ($CL_{int}$) are calculated using the equations below:

$$\text{Elimination rate constant } (k) = (-\text{gradient})$$

$$\text{Half-life } (t_{1/2})(\text{min}) = \frac{0.693}{k}$$

$$\text{Intrinsic clearance}(CL_{int})(\mu L/\text{min}/\text{million cells}) = \frac{V \times 0.693}{t_{1/2}}$$

where $V$ = Incubation volume (µL)/Number of cells

Two control compounds for each species are included in the assay and if the values for these compounds are not within the specified limits the results are rejected and the experiment repeated.

In Vivo Pharmacokinetics

In Vivo Studies

Experimental work was done in accordance with Home Office regulations under the Animals (Scientific Procedures) Act 1986, ICR ethical review processes and according to the UK National Cancer Research CRI Guidelines with local Ethical Committee approval (Workman, P.; Aboagye, E. O.; Balkwill, F.; Balmain, A.; Bruder, G.; Chaplin, D. J.; Double, J. A.; Everitt, J.; Farningham, D.; Glennie, M. J.; Kelland, L. R.; Robinson, V.; Stratford, I. J.; Tozer, G. M.; Watson, S.; Wedge, S. R.; Eccles, S. A. Guidelines for the welfare and use of animals in cancer research. Br. J. Cancer 2010, 102, 1555-1577).

Mouse Pharmacokinetics

Female Balb/C mice were obtained from Charles River (Margate, UK). Animals were adapted to laboratory conditions for at least 1 week prior to dosing and were allowed food and water adlibitum. Compounds were administered iv or po (0.1 mL/10 g) in 10% DMSO in 25% w/v hydroxypropyl beta cyclodextrin in 50 mM sodium citrate buffer. Blood samples were collected from the tail vein (20 µL) at 8 time points over 24 h post dosing and spotted onto Whatman FTA-DMPK B cards (VWR) together with a calibration curve and quality controls spiked in control blood. Cards were allowed to dry at room temperature for at least 2 h. 6 mm discs were punched from the cards and extracted with 200 µL methanol containing 500 nM olomoucine as an internal standard. Following centrifugation, extracts were analyzed by multiple reaction monitoring of precursor and product ions by LC-ESI-MS/MS on a QTRAP 4000 (Sciex, Warrington, UK) using a short gradient consisting of 0.1% formic acid and methanol on a Phenomenex (Macclesfield, UK) Kinetex™ C18, 5 cm×2.6 µm, 2.1 mm i.d UHPLC column. Pharmacokinetic parameters were derived from non-compartmental analysis using Phoenix (model 200 and 201) Pharsight WinNonlin® version 6.1/6.3.

Rat Pharmacokinetics

Female CD rats were obtained from Charles River (Margate, UK). Animals were adapted to laboratory conditions for at least 5 days prior to dosing and were allowed food and water ad libitum. Compounds were administered iv or po (1 ml/200 g) in 10% DMSO in 25% w/v hydroxypropyl beta cyclodextrin in 50 mM sodium citrate buffer. Blood samples were collected from the tail vein (20 µL) at 8 time points over 24 h post dosing and spotted onto Whatman FTA-DMPK B cards (VWR) together with a calibration curve and quality controls spiked in control blood. Cards were allowed to dry at room temperature for at least 2 h. 6 mm discs were punched from the cards and extracted with 200 µL methanol containing internal standard. Following centrifugation, extracts were analyzed by multiple reaction monitoring of precursor and product ions by LC-ESI-MS/MS on a QTRAP 4000 (Sciex, Warrington, UK) using a short gradient consisting of 0.1% formic acid and methanol on a Phenomenex (Macclesfield, UK) Kinetex™ C18, 5 cm×2.6 µm, 2.1 mm i.d UHPLC column. Pharmacokinetic parameters were derived from non-compartmental analysis using Phoenix (model 200 and 201) Pharsight WinNonlin® version 6.1/6.3.

Protein Binding

Protein binding was measured using Rapid Equilibrium Dialysis (RED, Thermo Fisher Scientific, Loughborough, UK). Plasma was obtained from either female Balb/C mice or female CD (SD) rats (Charles River, Margate, UK) and stored at −20° C. Cell culture media was DMEM (Sigma Aldrich, Dorset, UK) supplemented with 10% FCS (Invitrogen), 2 mmol/L of L-glutamine, and 1 x non-essential amino acids. The RED plate, buffer, plasma and media solutions were heated to 37° C. before dialysis. Test compound in DMSO was spiked into either diluted plasma (10-fold dilution in 100 mM phosphate buffer) or cell culture media as appropriate resulting in a concentration of 5 µM for dialysis, containing 1% DMSO. 300 µL of spiked diluted plasma or media was added to the donor side of the RED plate and 500 µL of 100 mM phosphate buffer was added to the receiver well. The plate was sealed with a gas-permeable lid and dialysis was performed by shaking for 4 h at 37° C. After dialysis, samples were transferred from the RED plate and donor and receiver samples were matrix matched followed by protein precipitation with methanol containing internal standard. Samples were mixed, centrifuged and supernatant was taken for analysis by ESI-LCMS/MS on a QTRAP 4000 (Sciex, Warrington, UK) using a short gradient consisting of 0.1% formic acid and methanol on a Phenomenex (Macclesfield, UK) Kinetex™ C18, 5 cm×2.6 µm, 2.1 mm i.d UHPLC column. The fraction unbound ($f_u$) was calculated as follows:

$$f'_u = \frac{PAR \text{ receiver}}{PAR \text{ donor}}$$

where $PAR$ = Peak Area Ratio of Analyte/Internal Standard.

$$f_u = 1 \bigg/ \left(1 + \left(\frac{1}{fu'} - 1\right) * \text{dilution factor}\right)$$

where dilution factor = 10 for plasma, 1 for media.

Blood to Plasma Ratio

Fresh blood was obtained from either female Balb/C mice or female CD (SD) rats (Charles River, Margate, UK) and an aliquot centrifuged to obtain plasma. Blood and plasma was pre-warmed to 37° C. Test compound was spiked into blood and plasma to a final concentration of 1 μM containing 1% of methanol:water and <0.1% DMSO. Spiked samples were incubated for 30 minutes at 37° C. Blood was then centrifuged to obtain plasma. Equal volumes of plasma from centrifuged blood and from original spiked plasma samples were protein precipitated with 10-fold methanol containing internal standard, mixed and centrifuged. Supernatant was taken for analysis by ESI-LCMS/MS on a QTRAP 4000 (Sciex, Warrington, UK) using a short gradient consisting of 0.1% formic acid and methanol on a Phenomenex (Macclesfield, UK) Kinetex™ C18, 5 cm×2.6 μm, 2.1 mm i.d UHPLC column. The blood to plasma ratio was calculated as:

$$\frac{PAR \text{ in Spiked Plasma}}{PAR \text{ in Plasma from Spiked Blood}}$$

where $PAR$ = Peak Area Ratio of Analyte/Internal Standard.

Results
Cellular Activity

In Vitro Metabolism

TABLE 2

Hepatocyte stability of deuterated compounds in an in vitro assay.

| Compound | Mouse Hepatocyte $CL_{int}^{a,b}$ | Rat Hepatocyte $CL_{int}^{a,b}$ | Dog Hepatocyte $CL_{int}^{a,b}$ | Human Hepatocyte $CL_{int}^{a,b}$ |
|---|---|---|---|---|
| Compound D (REF) | 42 | 38 | 31 (m); 40 (f)$^c$ | 9 |
| Compound A | 44 | 24 | 37 (m); 73 (f)$^c$ | 5 |
| Compound B | n.d.$^d$ | 38 | n.d.$^d$ | n.d.$^d$ |
| Compound C | 53 | 25 | 30 (m); 73 (f)$^c$ | 9 |

$^a$Mouse/Rat/Dog/Human hepatocyte stability assays were carried out at Cyprotex, n = 1. In vitro $CL_{int}$ is calculated from the half-life using standard procedures.
$^b CL_{int}$ values are reported in μL/min/10$^6$ cells.
$^c$m = male; f = female.
$^d$n.d. = not determined.

TABLE 1

Cellular activity of the deuterated compounds in SK-OV-3 ovarian cancer cell line.

| Compound | Structure | SK-OV-3 $pIC_{50}$ ± SEM $(n)^{a,b}$ | SK-OV-3 $pGI_{50}$ ± SEM $(n)^{a,c}$ |
|---|---|---|---|
| Compound D (REF) | 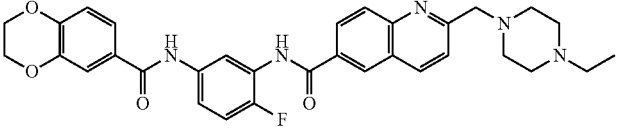 [SMILES: CCN1CCN(Cc2ccc3cc(C(=O)Nc4cc(NC(=O)c5ccc6c(c5)OCCO6)ccc4F)ccc3n2)CC1] | 7.04 ± 0.05 (36) | 8.07 ± 0.03 (44) |
| Compound A | 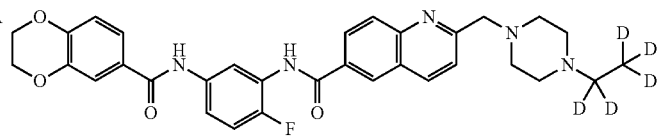 | 6.84 ± 0.10 (3) | 8.06 ± 0.06 (3) |
| Compound B | 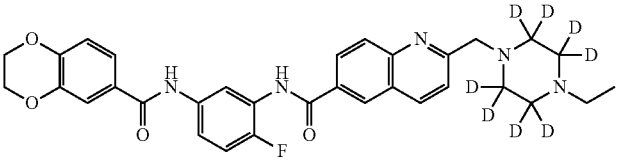 [SMILES: [2H]C1([2H])N(CC)C([2H])([2H])C([2H])([2H])N(Cc2ccc3cc(C(=O)Nc4cc(NC(=O)c5ccc6c(c5)OCCO6)ccc4F)ccc3n2)C1([2H])[2H]] | 6.09 ± 0.09 (3) | 7.74 ± 0.08 (5) |
| Compound C | 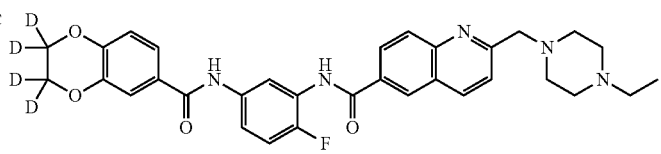 | 6.77 ± 0.16 (4) | 7.94 ± 0.03 (3) |

$^a$All results are quoted as the geometric mean ± SEM. $pIC_{50}/pGI_{50}$ = −log $IC_{50}/GI_{50}$ (M). The number of repeats, n, are described in parentheses.
$^b$Cell-based ELISA assay for inhibition of HSP72 induction; SK-OV-3 cells were pretreated with compound at the relevant concentration for 1 hour before the addition of 250 nM 17-AAG. HSP72 levels were then quantified after 18 hours.
$^c$Growth inhibition was measured after 96 hours of treatment and compared to vehicle control.

In Vivo Pharmacokinetics

TABLE 3

Mouse blood PK parameters for Compound D and Compound A.

| Compound | Dose po/iv (mg/Kg) | $AUC_{0-24\,h}^{PO}$ (hr * nM)$^a$ | Blood Cl (mL/min/Kg) | $V_{ss}$ (L/Kg) | $t_{1/2}$ (h) | F (%) |
|---|---|---|---|---|---|---|
| Compound D (REF) | 5/5 | 6050 | 10$^a$ | 1.9$^a$ | 4.1$^a$ | 42 |
| Compound A | 5/5 | 3700 | 12$^b$ | 1.7$^b$ | 3.4$^b$ | 30 |

All values are quoted to 2 SF.
$^a$The geometric mean of n = 3 individual mice.
$^b$The geometric mean of n = 5 individual mice.

TABLE 4

Rat blood PK parameters for Compound D and Compound A.

| Compound | Dose po/iv (mg/Kg) | $AUC_{0-24\,h}^{PO}$ (hr * nM)$^a$ | Blood Cl (mL/min/Kg)$^a$ | $V_{ss}$ (L/Kg)$^a$ | $t_{1/2}$ (h)$^a$ | F (%) |
|---|---|---|---|---|---|---|
| Compound D (REF) | 1/5 | 2600 | 24 | 7.3 | 3.1 | 45 |
| Compound A | 1/5 | 1070 | 25 | 5.6 | 3.5 | 20 |

All values are quoted to 2 SF.
$^a$The geometric mean of n = 3 individual rats.

TABLE 5

Mouse unbound PK parameters for Compound D and Compound A.

| Compound | Blood Cl (mL/min/Kg) | $V_{ss}$ (L/Kg) | $f_{ub}^{c}$ | $Cl_u^d$ (mL/min/Kg) | $V_{du}^e$ (L/Kg) | $t_{1/2}$ (h) | F (%) |
|---|---|---|---|---|---|---|---|
| Compound D (REF) | 10$^a$ | 1.9$^a$ | 0.012 | 833 | 158 | 4.1$^a$ | 42 |
| Compound A | 12$^b$ | 1.7$^b$ | 0.012 | 1000 | 140 | 3.4$^b$ | 30 |

The compounds were dosed @5 mg/Kg iv and po.
$^a$The geometric mean of n = 3 individual mice.
$^b$The geometric mean of n = 5 individual mice.
$^c f_{ub} = f_{up}/B{:}P$; for compound D $f_{up}$ = 0.0425 and B:P@1 µM = −3.50; for compound A $f_{up}$ = 0.0397 and B:P@1 µM = 3.23.
$^d Cl_u = Cl/f_{ub}$.
$^e V_{du} = V_{ss}/f_{ub}$.

TABLE 6

Rat unbound PK parameters for Compound D and Compound A.

| Compound | Blood Cl (mL/min/Kg)$^a$ | $V_{ss}$ (L/Kg)$^a$ | $f_{ub}^b$ | $Cl_u^c$ (mL/min/Kg) | $V_{du}^d$ (L/Kg) | $t_{1/2}$ (h)$^a$ | F (%) |
|---|---|---|---|---|---|---|---|
| Compound D (REF) | 24 | 7.3 | 0.032 | 750 | 228 | 3.1 | 45 |
| Compound A | 25 | 5.6 | 0.040 | 625 | 140 | 3.5 | 20 |

The compounds were dosed @1 mg/Kg iv and @5 mg/Kg po.
$^a$The geometric mean of n = 3 individual rats.
$^b f_{ub} = f_{up}/B{:}P$; for compound D $f_{up}$ = 0.0344 and B:P@1 µM = 1.07; for compound A $f_{up}$ = 0.0365 and B:P@1 µM = 0.92.
$^c Cl_u = Cl/f_{ub}$.
$^d V_{du} = V_{ss}/f_{ub}$.

DISCUSSION

Compound A showed potent cellular activity in SK-OV-3 ovarian cancer cell line and improved in vitro properties in a human hepatocyte stability assay when compared to the reference Compound D. The present invention therefore provides agents capable of inhibiting HSF1 with improved ADME properties, indicating suitability for in vivo administration to humans. In contrast, Compound A did not show any ADME advantage in vivo when compared in rat and mouse to Compound D. However, it is known in the art that metabolic switching is very complex, and that it may occur differentially both between different animal models, and also between animal models and humans as studies translate from the preclinical to clinical stages (Drug Metab Dispos. 2012; 40(3):625-34). The lack of benefit in mouse and rat in vivo is therefore not indicative of lack of benefit in humans in vivo. Moreover, the art makes clear that metabolically active hepatocytes are the closest in vitro surrogate for in vivo hepatic metabolism (Eur J Drug Metab Pharmacokinet 1990; 15:165-171). Therefore, the improved human hepatocyte stability is an indicator of improved human in vivo hepatic metabolism, indicating suitability for in vivo administration to humans. From the in vitro hepatocyte data compound D has a predicted unbound human clearance of 54 mL/min/Kg while compound A has a predicted unbound human clearance of 30 mL/min/Kg, therefore predicting a 2-fold improvement in human unbound clearance.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise paragraphed. No language in the specification should be construed as indicating any non-paragraphed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the paragraphs appended hereto as permitted by applicable law.

The invention claimed is:

1. A compound of formula (I), or a pharmaceutically acceptable salt or solvate thereof,

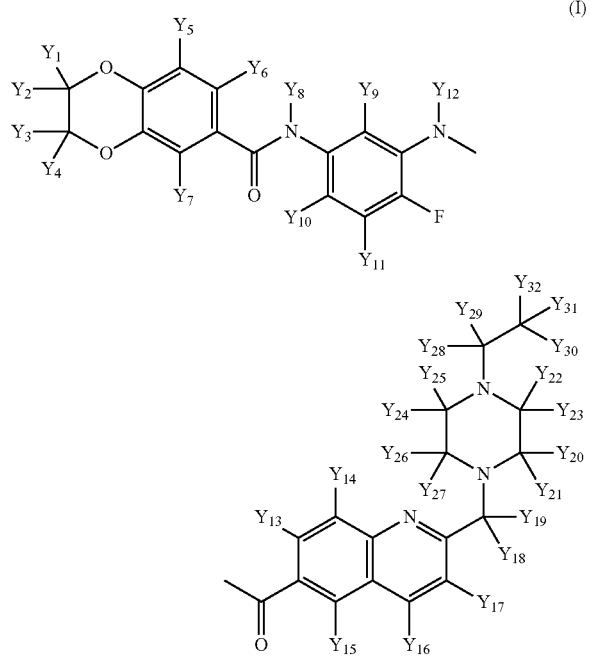

(I)

wherein:

$Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are independently selected from hydrogen or deuterium, provided that at least one of $Y_1$, $Y_2$, $Y_3$, $Y_4$, $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ is deuterium.

2. A compound of formula (I), or a pharmaceutically acceptable salt or solvate thereof, according to claim 1 wherein $Y_8$ and $Y_{12}$ are hydrogen.

3. A compound of formula (I), or a pharmaceutically acceptable salt or solvate thereof, according to claim 1 wherein at least 2, 3, 4, 5, 6, 7, or 8 of $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$, and $Y_{32}$ are deuterium.

4. A compound of formula (I), or a pharmaceutically acceptable salt or solvate thereof, according to claim 1 wherein from 2 to 8 of $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$, and $Y_{32}$ are deuterium.

5. A compound of formula (I), or a pharmaceutically acceptable salt or solvate thereof, according to claim 1 wherein $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$ and $Y_{17}$ are hydrogen; and $Y_1$, $Y_2$, $Y_3$, $Y_4$, $Y_{18}$, $Y_{19}$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are independently selected from hydrogen and deuterium.

6. A compound of formula (I), or a pharmaceutically acceptable salt or solvate thereof, according to claim 1, wherein $Y_5$, $Y_6$, $Y_7$, $Y_8$, $Y_9$, $Y_{10}$, $Y_{11}$, $Y_{12}$, $Y_{13}$, $Y_{14}$, $Y_{15}$, $Y_{16}$, $Y_{17}$, $Y_{18}$ and $Y_{19}$ are hydrogen; and $Y_1$, $Y_2$, $Y_3$, $Y_4$, $Y_{20}$, $Y_{21}$, $Y_{22}$, $Y_{23}$, $Y_{24}$, $Y_{25}$, $Y_{26}$, $Y_{27}$, $Y_{28}$, $Y_{29}$, $Y_{30}$, $Y_{31}$ and $Y_{32}$ are independently selected from hydrogen and deuterium.

7. A compound of formula (I), or a pharmaceutically acceptable salt or solvate thereof, according to claim 1 wherein $Y_1$ and $Y_2$ are deuterium.

8. A compound of formula (I), or a pharmaceutically acceptable salt or solvate thereof, according to claim 1 wherein $Y_3$ and $Y_4$ are deuterium.

9. A compound of formula (I), or a pharmaceutically acceptable salt or solvate thereof, according to claim 1 wherein $Y_{18}$ and $Y_{19}$ are deuterium.

10. A compound of formula (I), or a pharmaceutically acceptable salt or solvate thereof, according to claim 1 wherein $Y_{24}$, $Y_{25}$, $Y_{26}$ and $Y_{27}$ are deuterium.

11. A compound of formula (I), or a pharmaceutically acceptable salt or solvate thereof, according to claim 1 wherein $Y_{20}$, $Y_{21}$, $Y_{23}$ and $Y_{24}$ are deuterium.

12. A compound of formula (I), or a pharmaceutically acceptable salt or solvate thereof, according to claim 1 wherein $Y_{20}$, $Y_{21}$, $Y_{26}$ and $Y_{27}$ are deuterium.

13. A compound of formula (I), or a pharmaceutically acceptable salt or solvate thereof, according to claim 1 wherein $Y_{22}$, $Y_{23}$, $Y_{24}$ and $Y_{25}$ are deuterium.

14. A compound of formula (I), or a pharmaceutically acceptable salt or solvate thereof, according to claim 1 wherein $Y_{28}$ and $Y_{29}$ are deuterium.

15. A compound of formula (I), or a pharmaceutically acceptable salt or solvate thereof, according to claim 1 wherein $Y_{30}$, $Y_{31}$ and $Y_{32}$ are deuterium.

16. A compound of formula (I), or a pharmaceutically acceptable salt or solvate thereof, according to claim 1 selected from:

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| $Y_1$ | D | H | D | H | H | H | H | H | H | H | H | D | D | D | D | D | H | H | D | D |
| $Y_2$ | D | H | D | H | H | H | H | H | H | H | H | D | D | D | D | D | H | H | D | D |
| $Y_3$ | H | D | D | H | H | H | H | H | H | H | H | D | D | D | D | D | H | H | D | D |
| $Y_4$ | H | D | D | H | H | H | H | H | H | H | H | D | D | D | D | D | H | H | D | D |
| $Y_5$ | H | H | H | H | H | H | H | H | H | H | H | H | H | H | H | H | H | H | H | H |
| $Y_6$ | H | H | H | H | H | H | H | H | H | H | H | H | H | H | H | H | H | H | H | H |
| $Y_7$ | H | H | H | H | H | H | H | H | H | H | H | H | H | H | H | H | H | H | H | H |
| $Y_8$ | H | H | H | H | H | H | H | H | H | H | H | H | H | H | H | H | H | H | H | H |
| $Y_9$ | H | H | H | H | H | H | H | H | H | H | H | H | H | H | H | H | H | H | H | H |
| $Y_{10}$ | H | H | H | H | H | H | H | H | H | H | H | H | H | H | H | H | H | H | H | H |
| $Y_{11}$ | H | H | H | H | H | H | H | H | H | H | H | H | H | H | H | H | H | H | H | H |
| $Y_{12}$ | H | H | H | H | H | H | H | H | H | H | H | H | H | H | H | H | H | H | H | H |
| $Y_{13}$ | H | H | H | H | H | H | H | H | H | H | H | H | H | H | H | H | H | H | H | H |
| $Y_{14}$ | H | H | H | H | H | H | H | H | H | H | H | H | H | H | H | H | H | H | H | H |
| $Y_{15}$ | H | H | H | H | H | H | H | H | H | H | H | H | H | H | H | H | H | H | H | H |
| $Y_{16}$ | H | H | H | H | H | H | H | H | H | H | H | H | H | H | H | H | H | H | H | H |
| $Y_{17}$ | H | H | H | H | H | H | H | H | H | H | H | H | H | H | H | H | H | H | H | H |
| $Y_{18}$ | H | H | H | H | H | H | H | H | H | D | D | D | H | D | H | D | H | D | H | D |
| $Y_{19}$ | H | H | H | H | H | H | H | H | H | D | D | D | H | D | H | D | H | D | H | D |
| $Y_{20}$ | H | H | H | D | H | D | H | H | H | H | H | H | H | D | D | D | D | D | D | D |
| $Y_{21}$ | H | H | H | D | H | D | H | H | H | H | H | H | H | D | D | D | D | D | D | D |
| $Y_{22}$ | H | H | H | H | D | D | H | H | H | H | H | H | H | D | D | D | D | D | D | D |
| $Y_{23}$ | H | H | H | H | D | D | H | H | H | H | H | H | H | D | D | D | D | D | D | D |
| $Y_{24}$ | H | H | H | D | D | D | H | H | H | H | H | H | H | D | D | D | D | D | D | D |
| $Y_{25}$ | H | H | H | D | D | D | H | H | H | H | H | H | H | D | D | D | D | D | D | D |
| $Y_{26}$ | H | H | H | D | H | D | H | H | H | H | H | H | H | D | D | D | D | D | D | D |
| $Y_{27}$ | H | H | H | D | H | D | H | H | H | H | H | H | H | D | D | D | D | D | D | D |
| $Y_{28}$ | H | H | H | H | H | H | D | H | D | H | D | D | D | D | H | H | D | D | D | D |
| $Y_{29}$ | H | H | H | H | H | H | D | H | D | H | D | D | D | D | H | H | D | D | D | D |
| $Y_{30}$ | H | H | H | H | H | H | D | D | H | D | H | D | D | D | H | H | D | D | D | D |
| $Y_{31}$ | H | H | H | H | H | H | D | D | H | D | H | D | D | D | H | H | D | D | D | D |
| $Y_{32}$ | H | H | H | H | H | H | H | D | D | H | D | D | D | D | H | H | D | D | D | D. |

17. A compound, or a pharmaceutically acceptable salt or solvate thereof, selected from:

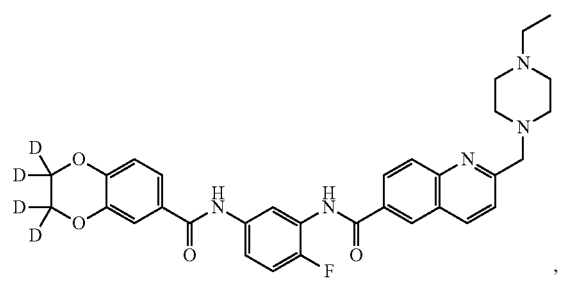

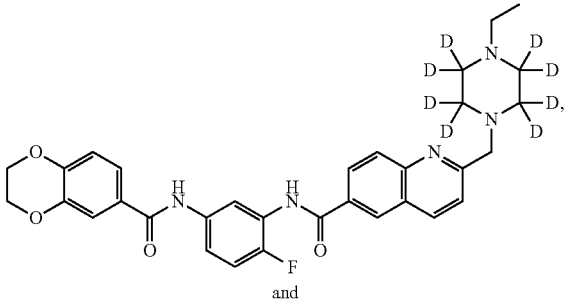
and

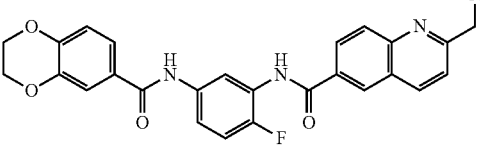

18. A pharmaceutical composition comprising a compound according to claim 1, or a pharmaceutically acceptable salt or solvate thereof, in admixture with a pharmaceutically acceptable diluent or carrier.

19. A method of treating a HSF1-mediated condition or disease in a patient in need of such treatment, said method comprising administering to said patient a therapeutically effective amount of a compound according to claim 1, or a pharmaceutically acceptable salt or solvate thereof.

20. The method of claim 19, wherein the HSF1-mediated condition or disease is a cancer, autoimmune disease or a viral disease.

\* \* \* \* \*